US010058311B1

(12) United States Patent
Insignares et al.

(10) Patent No.: US 10,058,311 B1
(45) Date of Patent: *Aug. 28, 2018

(54) ERGONOMIC MULTI-FUNCTIONAL HANDLE FOR USE WITH A MEDICAL INSTRUMENT

(71) Applicants: Rogelio A. Insignares, Winter Park, FL (US); Daniel Glenn Doerr, Orlando, FL (US); Roland Strelitzki, Altamonte Springs, FL (US); Gary Wayne Haberland, Winter Park, FL (US); John A. Farnella, Jr., Orlando, FL (US); Kenneth M. Roger, Casselberry, FL (US)

(72) Inventors: Rogelio A. Insignares, Winter Park, FL (US); Daniel Glenn Doerr, Orlando, FL (US); Roland Strelitzki, Altamonte Springs, FL (US); Gary Wayne Haberland, Winter Park, FL (US); John A. Farnella, Jr., Orlando, FL (US); Kenneth M. Roger, Casselberry, FL (US)

( * ) Notice: Subject to any disclaimer, the term of this patent is extended or adjusted under 35 U.S.C. 154(b) by 703 days.

This patent is subject to a terminal disclaimer.

(21) Appl. No.: 14/050,294

(22) Filed: Oct. 9, 2013

(51) Int. Cl.
*A61B 17/00* (2006.01)
(52) U.S. Cl.
CPC .................................. *A61B 17/00* (2013.01)
(58) Field of Classification Search
CPC .............. A61B 17/00; A61B 17/00234; A61B 17/0218; A61B 17/0469; A61B 17/12013; A61B 17/1285; A61B 17/29; A61B 2017/00265

USPC ..................... 606/1, 130, 135–148, 205–211
See application file for complete search history.

(56) References Cited

U.S. PATENT DOCUMENTS

| | | | |
|---|---|---|---|
| 4,566,437 A | 1/1986 | Yamaguchi et al. | |
| 4,616,630 A | 10/1986 | Arakawa et al. | |
| 4,896,661 A | 1/1990 | Bogert et al. | |
| 5,085,661 A | 2/1992 | Moss et al. | |
| 5,168,864 A | 12/1992 | Shockey et al. | |
| 5,474,057 A | 12/1995 | Makiwer et al. | |
| 5,476,479 A | 12/1995 | Green et al. | |
| 5,483,952 A | 1/1996 | Aranyi et al. | |
| 5,626,608 A * | 5/1997 | Cuny ................. | A61B 17/2909 600/131 |

(Continued)

*Primary Examiner* — Ahmed Farah
(74) *Attorney, Agent, or Firm* — Ashkan Najafi

(57) ABSTRACT

A multi-functional handle manipulates a medical instrument and includes a body capable of being gripped by a hand of a user and further capable of being in communication with the medical instrument. In non-limiting exemplary embodiments, the handle may include one or more of a first trigger assembly, a second trigger assembly and a third trigger assembly. Non-limiting exemplary embodiments also include one or more of a primary digit-receiving member, a secondary digit-receiving member, and a tertiary digit-supporting member for facilitating ergonomic operation of the handle. The actuation arm actuates the medical instrument independently from movement of the primary digit-receiving member wherein the primary digit-receiving member can be selectively displaced between alternate orientations relative to a position of the body and relative to a position of the actuation arm, respectively, without affecting manipulation of the medical instrument.

20 Claims, 25 Drawing Sheets

(56) References Cited

U.S. PATENT DOCUMENTS

| | | | |
|---|---|---|---|
| 5,659,959 A | 8/1997 | Parlowski et al. | |
| 5,683,349 A | 11/1997 | Makower et al. | |
| 5,785,644 A | 7/1998 | Grabover et al. | |
| 5,830,231 A | 11/1998 | Geiges, Jr. et al. | |
| 6,077,286 A | 6/2000 | Cuschieri et al. | |
| 6,129,740 A | 10/2000 | Michelson et al. | |
| 6,168,605 B1 * | 1/2001 | Measamer | A61B 17/320016 606/170 |
| 6,217,511 B1 | 4/2001 | Held | |
| D449,499 S | 10/2001 | Voges et al. | |
| 6,299,624 B1 | 10/2001 | Cuschieri et al. | |
| 6,299,625 B1 | 10/2001 | Bacher et al. | |
| D457,958 S | 5/2002 | Dycus et al. | |
| D458,368 S | 6/2002 | Berberich et al. | |
| D458,370 S | 6/2002 | Berberich et al. | |
| 6,428,530 B1 | 8/2002 | Matern et al. | |
| 6,508,758 B2 | 1/2003 | Komi et al. | |
| 6,524,238 B2 | 2/2003 | Velikaris et al. | |
| 6,605,036 B1 | 8/2003 | Wild et al. | |
| 6,609,322 B1 | 8/2003 | Michelson et al. | |
| 6,666,854 B1 | 12/2003 | Lange et al. | |
| 6,679,834 B2 | 1/2004 | Stahl et al. | |
| 7,014,638 B2 | 3/2006 | Michelson et al. | |
| 7,087,071 B2 | 8/2006 | Nicholas et al. | |
| D531,311 S | 10/2006 | Guerra et al. | |
| D535,027 S | 1/2007 | James et al. | |
| 7,367,939 B2 | 5/2008 | Smith et al. | |
| 7,398,579 B2 | 7/2008 | Moshenrose et al. | |
| D575,401 S | 8/2008 | Hixson et al. | |
| D594,982 S | 6/2009 | Stefan et al. | |
| D610,259 S | 2/2010 | Way et al. | |
| 7,666,201 B2 | 2/2010 | Grayzel et al. | |
| D611,146 S | 3/2010 | Way et al. | |
| 7,708,756 B2 | 5/2010 | Nobis et al. | |
| D621,040 S | 8/2010 | Held et al. | |
| D621,503 S | 8/2010 | Otten et al. | |
| 7,765,646 B2 | 8/2010 | Oei et al. | |
| 7,789,825 B2 | 9/2010 | Nobis et al. | |
| 7,862,503 B2 | 1/2011 | Smith et al. | |
| D643,115 S | 8/2011 | Gonzales et al. | |
| 8,057,499 B2 | 11/2011 | Grayzel et al. | |
| 8,080,004 B2 | 12/2011 | Downey et al. | |
| 8,114,076 B2 | 2/2012 | Markham et al. | |
| 8,157,817 B2 | 4/2012 | Bonadio et al. | |
| D668,337 S | 10/2012 | Schurg et al. | |
| D670,378 S | 11/2012 | Connel et al. | |
| D670,379 S | 11/2012 | D'Lima et al. | |
| D670,380 S | 11/2012 | Sapalev et al. | |
| 8,366,604 B2 | 2/2013 | Konstorum et al. | |
| 2002/0069484 A1 | 6/2002 | Creel | |
| 2002/0087170 A1 * | 7/2002 | Kuhns | A61B 17/064 606/143 |
| 2005/0033337 A1 * | 2/2005 | Muir | A61B 17/320092 606/167 |
| 2005/0149016 A1 | 7/2005 | Rizvi | |
| 2007/0101547 A1 | 5/2007 | Egeland et al. | |
| 2007/0249903 A1 | 10/2007 | Ohashi et al. | |
| 2007/0265497 A1 | 11/2007 | Brown et al. | |
| 2008/0125762 A1 | 5/2008 | Hiller | |
| 2009/0299141 A1 | 12/2009 | Downey et al. | |
| 2010/0076260 A1 | 3/2010 | Taylor et al. | |
| 2010/0286480 A1 | 11/2010 | Peine et al. | |
| 2011/0065992 A1 * | 3/2011 | Bissinger | A61B 17/2909 600/131 |
| 2011/0112366 A1 * | 5/2011 | Basit | A61B 18/1445 600/131 |
| 2012/0209254 A1 | 8/2012 | Park et al. | |
| 2012/0220987 A1 | 8/2012 | Amann et al. | |
| 2012/0245414 A1 | 9/2012 | Verbeek et al. | |

\* cited by examiner

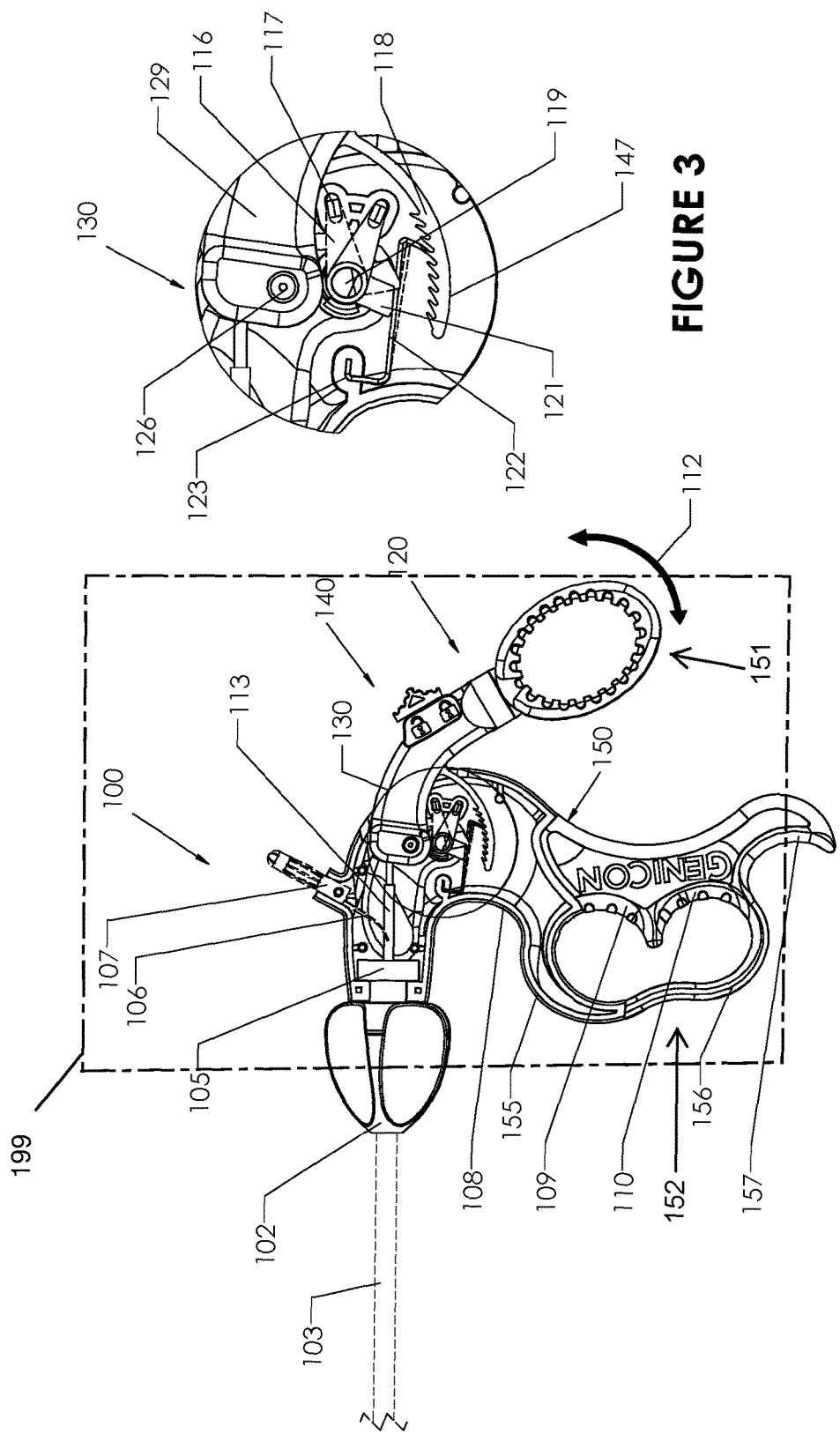

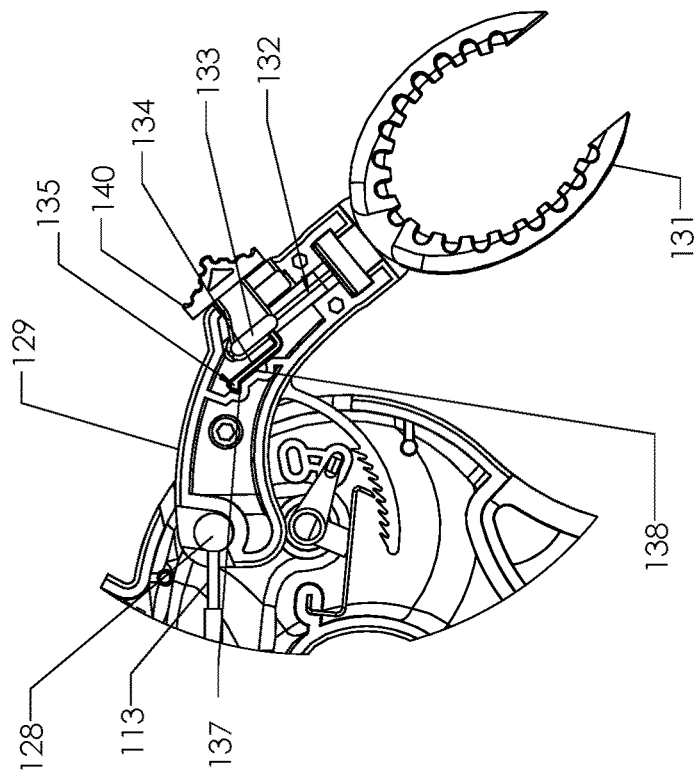
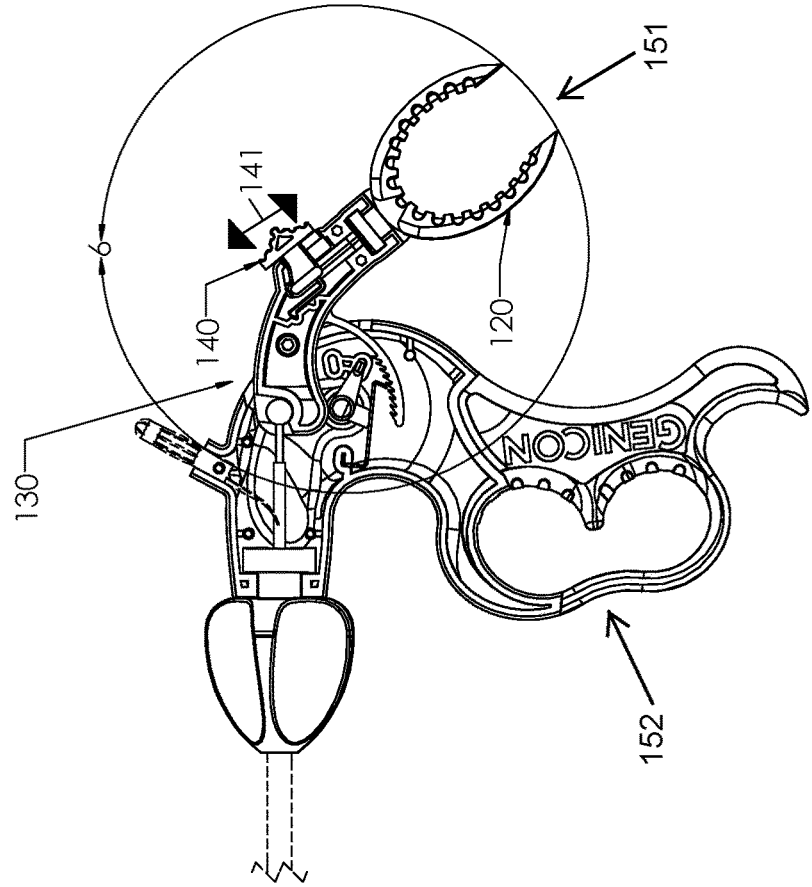
FIGURE 6
FIGURE 5

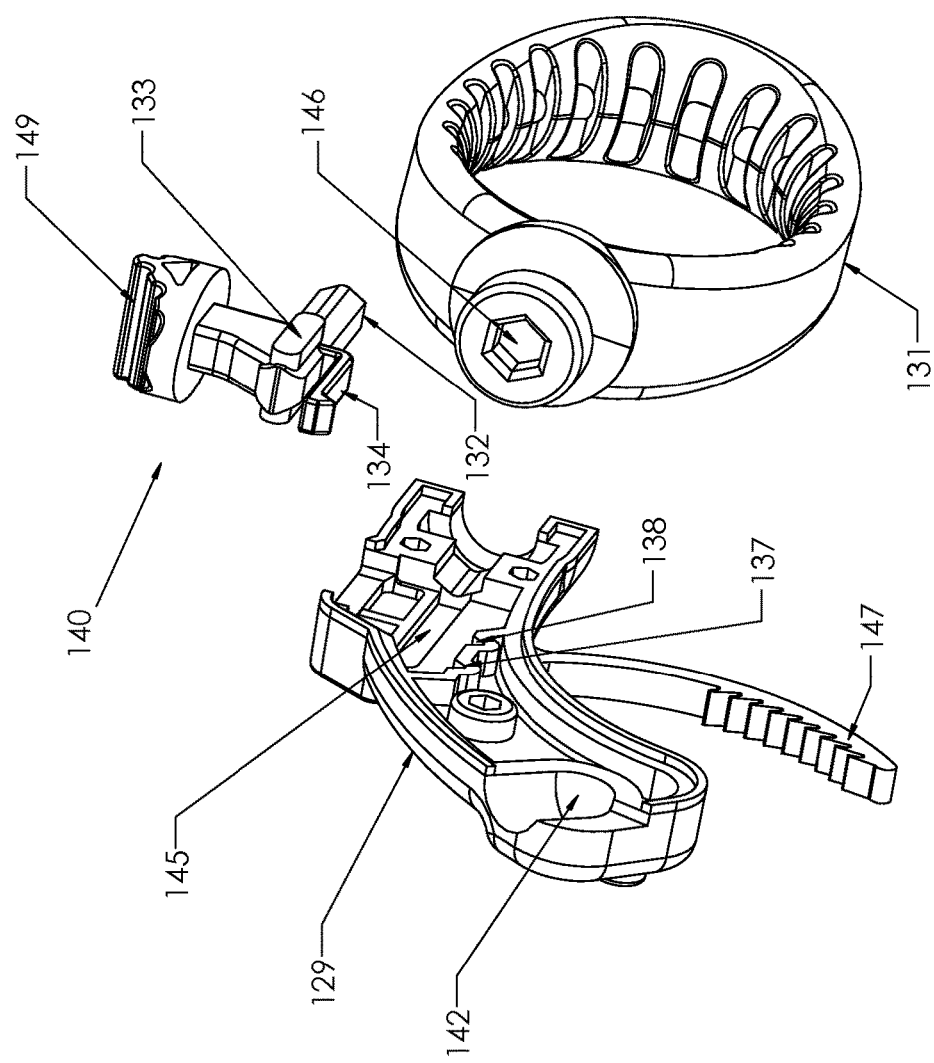

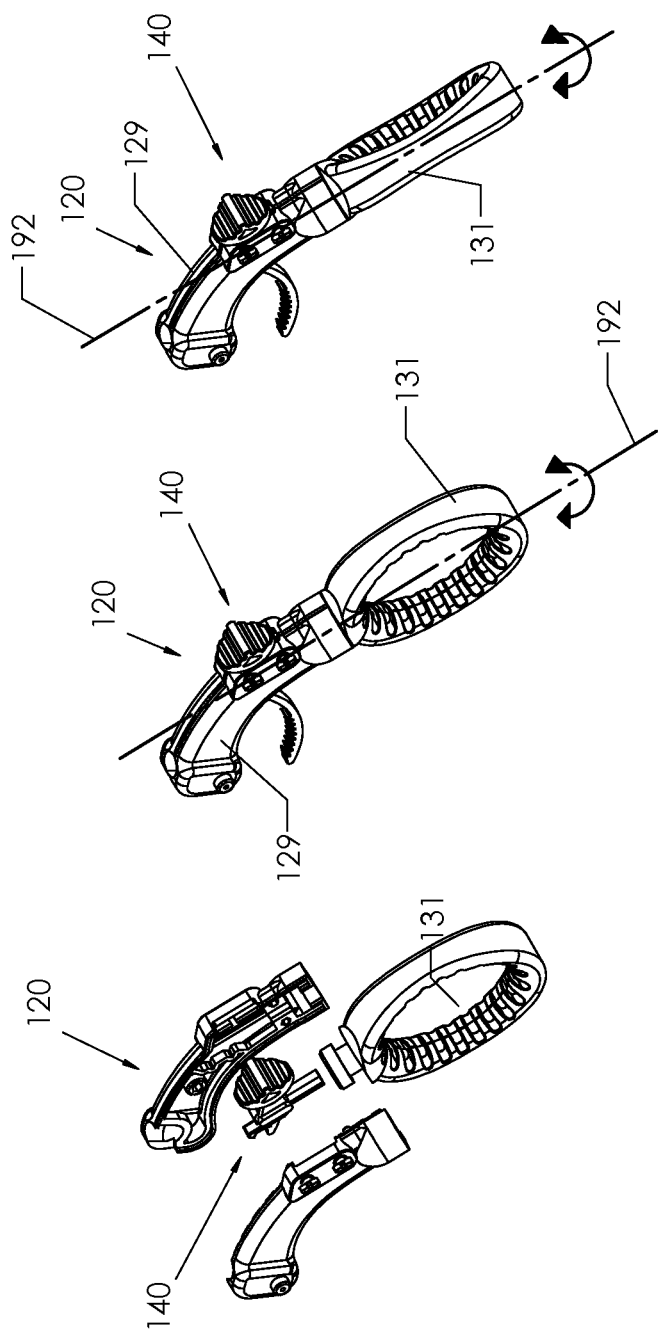

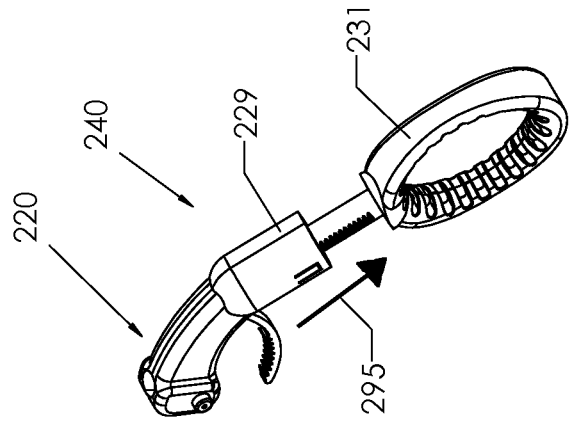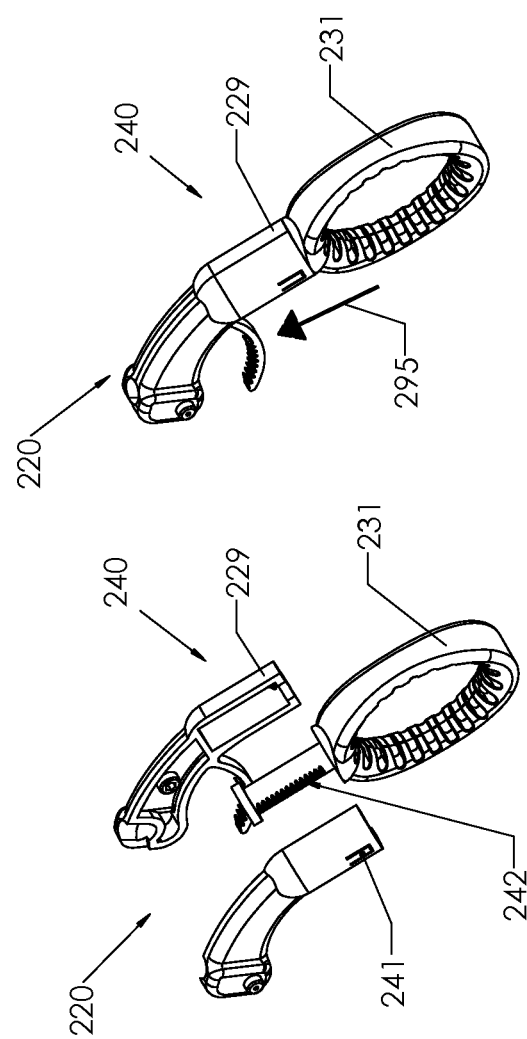

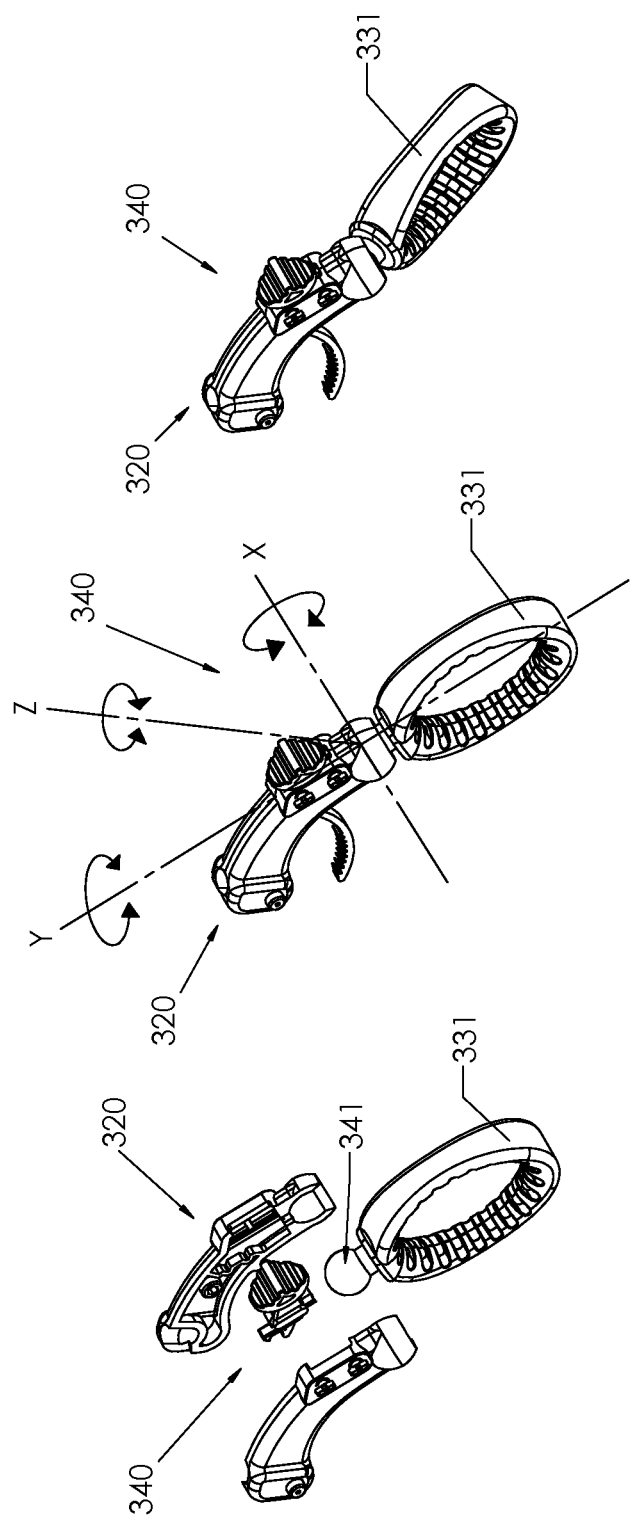

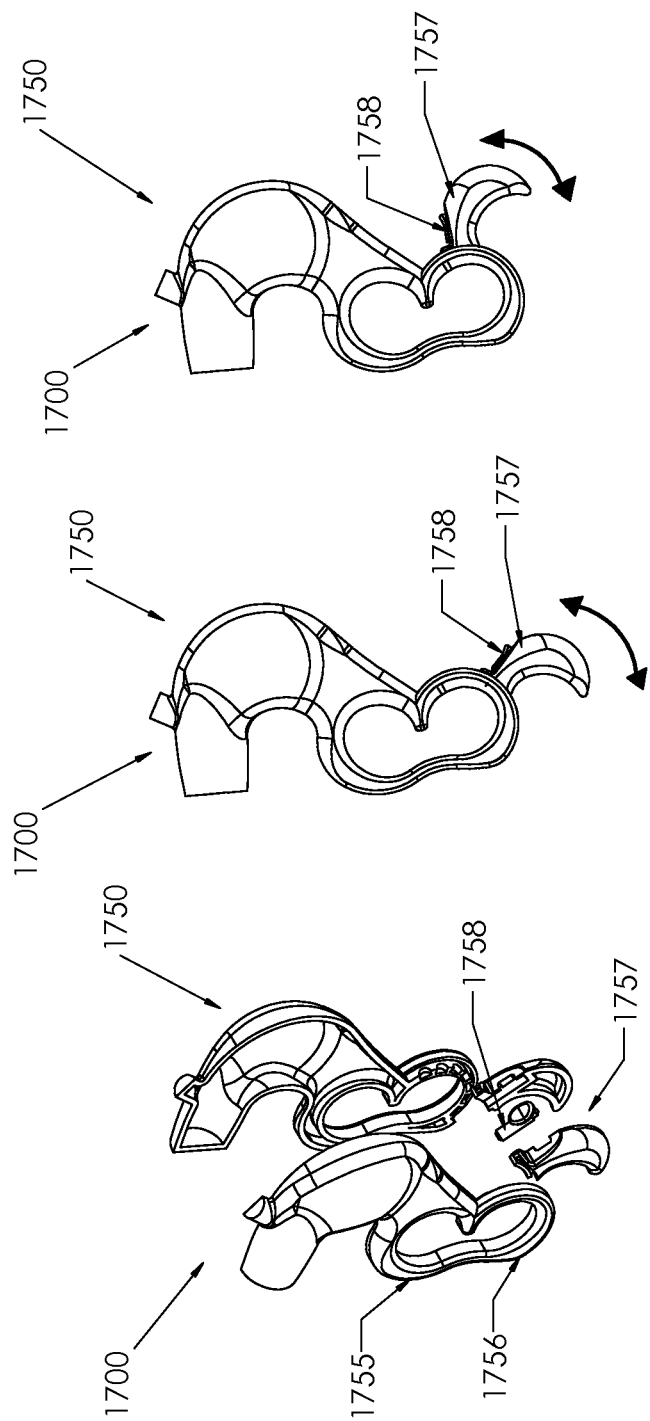

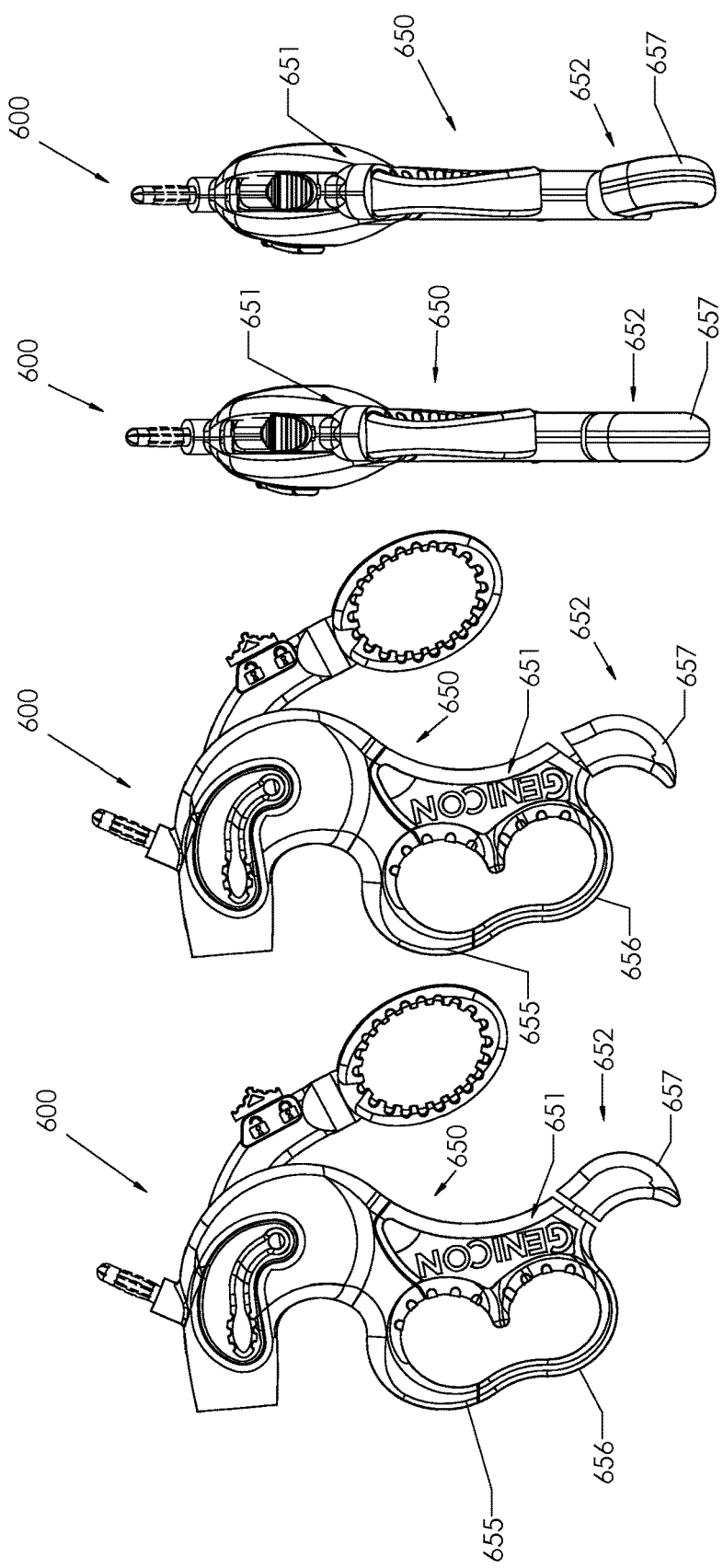

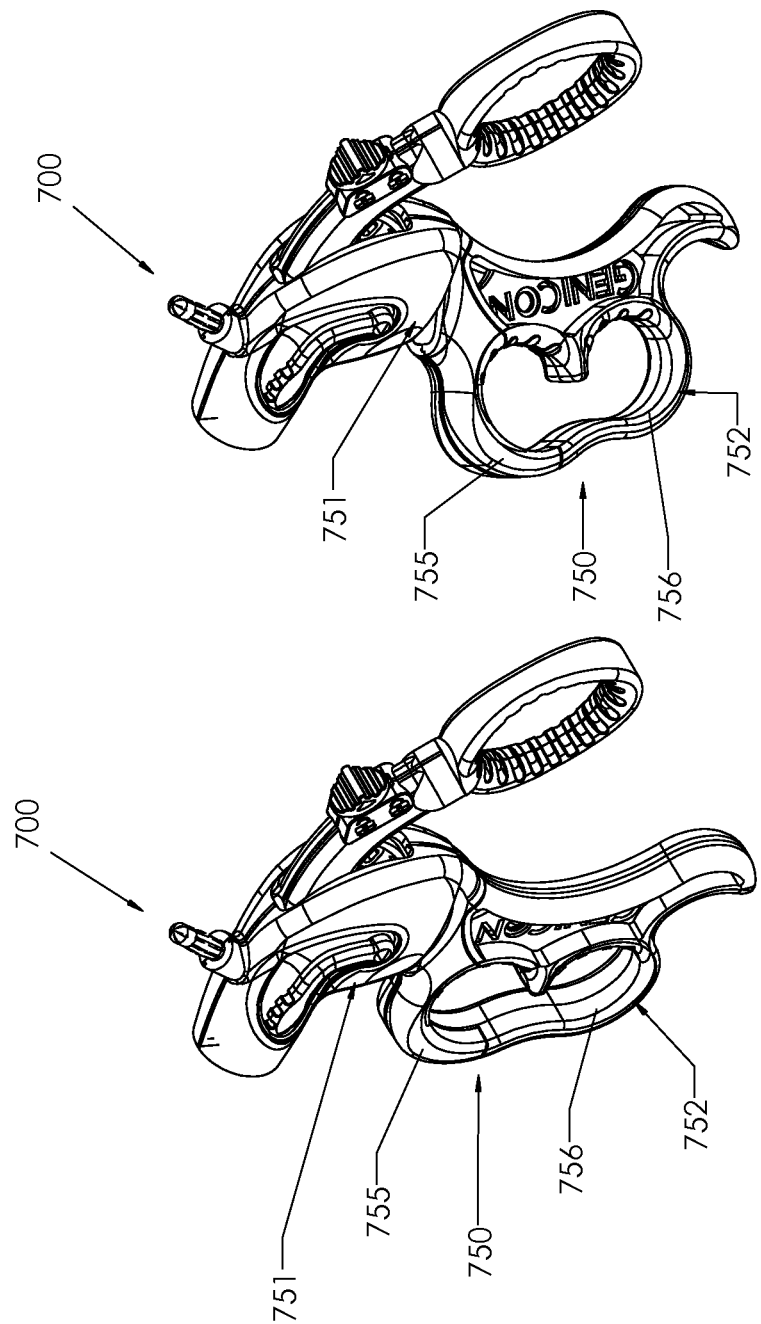

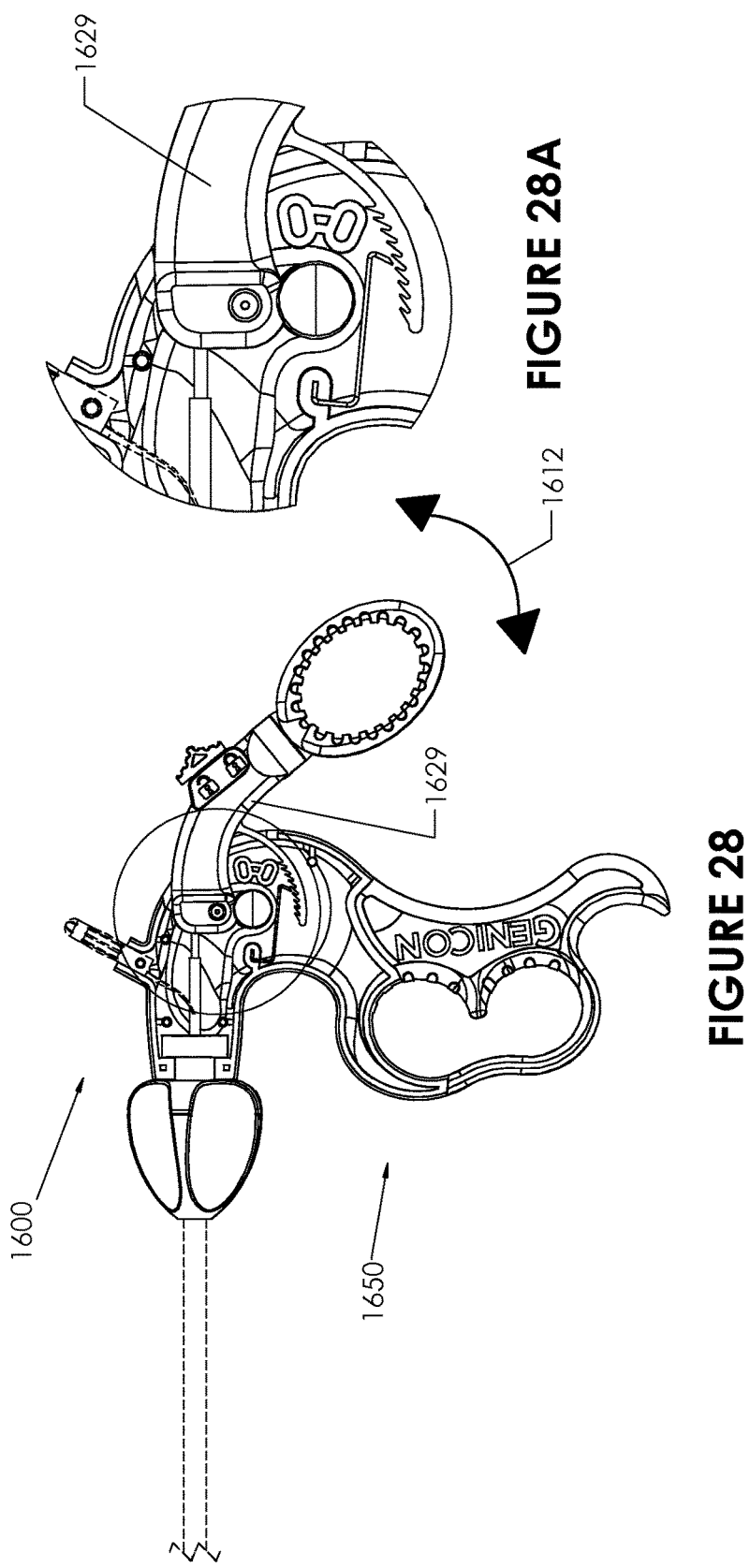

ERGONOMIC MULTI-FUNCTIONAL HANDLE FOR USE WITH A MEDICAL INSTRUMENT

CROSS REFERENCE TO RELATED APPLICATIONS

Not Applicable.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF NON-LIMITING EXEMPLARY EMBODIMENT(S) OF THE PRESENT DISCLOSURE

Technical Field

These non-limiting exemplary embodiment(s) relates to medical instrument handles and, more particularly, to an ergonomic multi-functional handle used to manipulate a medical instrument such as an electrosurgical, monopolar, laparoscopic instrument, for example, while reducing user fatigue.

Prior Art

Surgery is a learned skill requiring many years of training to develop an understanding of medical procedures, disease processes and healing that far exceed the basic medical principles. The surgeon must develop hand-to-eye coordination and acquire skills utilizing a variety of highly specialized medical instruments. The medical instruments and tools are an extension of the surgeon's hand. The surgeon's ability to perform the medical procedures with instruments and tools designed to benefit skill is paramount to the successful outcome for the patient. To enhance the medical performance to better serve the patient means developing instrument handles which are responsive, sensitive and ergonomically designed to benefit the natural motions of the human hand.

For example, laparoscopic instruments have been heavily developed for use by surgeons during medical procedures since around 1980s. There are many advantages of laparoscopic surgery compared with open procedure. These advantages include: reduced hemorrhaging which reduces needing a blood transfusion, smaller incision which reduces pain and shortens the recovery time of the patient, reduced scarring, reduced chances of needing pain medication, reduced hospital stays and quicker return to everyday life, and reduced risk of contamination and infection. Disadvantages of a laparoscopic procedure include: limited range of motion in the medical site, poor depth perception by the surgeon, and often laparoscopic tools are not perceived as moving in the same direction as the surgeon's hands.

In a variety of medical devices used for a diversity of medical or non-medical procedures, devices are designed with a dedicated handle or proximal end and a distal or actuation end. Typically medical device handles prescribe how they will be held in the hand by the layout of their handle shape or position of digit retaining portions. In instruments that contain loops, such as can be found in scissors type devices or grasping type devices, the loops are used for opening and closing the end effector, whether that is a scissors, grasper, clamp or similar device. In medical devices and more specifically minimally invasive or laparoscopic devices, a wide variety of angles of use can be generated. Typically a digit-looped device locks the digits and hand into a single orientation that can only function comfortably across a limited range of angles. Both in angles distal or away from the user and oblique angles or angles acutely to the side of the user, devices with digit loops move beyond their effective comfort range and promote hand stress and fatigue. This stress and discomfort is the result of creating unnatural hand postures. These hand postures can create severe wrist adduction or flexion causing discomfort and a loss of strength or leverage to operate the device. In certain instruments such as instruments used for minimally invasive or laparoscopic dissection, a surgeon may operate a looped device for long periods of time, across a wide range of angles.

In other conventional instruments, the handle comprises two holes for insertion of middle digit in one ring and digit in the other ring. The sizes of these rings are often small and not optimized for all types of hand sizes. This method in which the whole instrument is supported by only a thumb and finger and in which case, the hand and wrists make a very awkward and unnatural angle with respect to the angle of use is often very cumbersome to the surgeon and extended use of instrument in this position causes severe fatigue and hand pain. This results in painful situations during extended surgeries.

Accordingly, a need remains for an ergonomic medical instrument handle to overcome at least one of the above-noted shortcomings. The non-limiting exemplary embodiment(s) satisfies such a need by providing an ergonomic medical instrument handle that is convenient and easy to use, lightweight yet durable in design, versatile in its applications, and designed for easily and conveniently enabling a user to articulate his/her digit while operating the medical instrument handle and thereby reduce fatigue and discomfort during extended medical procedures.

BRIEF SUMMARY OF NON-LIMITING EXEMPLARY EMBODIMENT(S) OF THE PRESENT DISCLOSURE

In view of the foregoing background, it is therefore an object of the non-limiting exemplary embodiment(s) to provide an ergonomic multi-functional handle used to manipulate a medical instrument such as an electrosurgical, monopolar, laparoscopic instrument, for example, while reducing user fatigue. These and other objects, features, and advantages of the non-limiting exemplary embodiment(s) are provided by a multi-functional handle including a body having a centrally-registered longitudinal plane and capable of being gripped by an object (e.g., by a hand of a user, controller, etc.). The handle further includes a first trigger assembly coupled to the body. Such a first trigger assembly includes an actuation arm and a primary digit-receiving member in communication with the actuation arm. The primary digit-receiving member is selectively displaced between alternate orientations relative to a position of the body and relative to a position of the actuation arm, respectively. In this manner, the actuation arm is capable of actuating the medical instrument independently from movement of the primary digit-receiving member.

In a non-limiting exemplary embodiment, the handle further includes a second trigger assembly operatively coupled to the first trigger assembly in such a manner that the actuation arm is selectively displaced at alternate positions generally coplanar with the centrally-registered longitudinal plane of the body.

In a non-limiting exemplary embodiment, the first trigger assembly is pivotal about a first pivot axis wherein the second trigger assembly is pivotal about a second pivot axis wherein each of the first and second pivot axes are offset and traverse the centrally-registered longitudinal plane of the body.

In a non-limiting exemplary embodiment, the primary digit-receiving member is adjustably positioned about a proximal end of the actuation arm.

In a non-limiting exemplary embodiment, the actuation arm is displaced along a first path generally coplanar with the centrally-registered longitudinal plane of the body.

In a non-limiting exemplary embodiment, the primary digit-receiving member is simultaneously displaced relative to the actuation arm while the first trigger assembly is articulated about the first pivot axis.

In a non-limiting exemplary embodiment, the primary digit-receiving member is a loop capable of receiving a digit of the user while the user grasps the body.

In a non-limiting exemplary embodiment, the primary digit-receiving member is an incomplete loop capable of receiving a digit of the user while the user grasps the body.

In a non-limiting exemplary embodiment, the primary digit-receiving member has a linear shape capable of supporting a digit of the user while the user grasps the body and the actuation arm is articulated along a first path.

In a non-limiting exemplary embodiment, the primary digit-receiving member is registered parallel to the centrally-registered longitudinal plane of the body.

In a non-limiting exemplary embodiment, the primary digit-receiving member is registered oblique to the centrally-registered longitudinal plane of the body.

In a non-limiting exemplary embodiment, the primary digit-receiving member is registered orthogonal to the centrally-registered longitudinal plane of the body.

In a non-limiting exemplary embodiment, the actuation arm includes a ratchet arm statically connected thereto.

In a non-limiting exemplary embodiment, the ratchet arm is monolithically formed with the actuation arm.

In a non-limiting exemplary embodiment, the ratchet arm is coplanar with the centrally-registered longitudinal plane of the body.

In a non-limiting exemplary embodiment, the ratchet arm is integrally mated to the actuation arm.

In a non-limiting exemplary embodiment, the ratchet arm remains fixedly coupled to the actuation arm during articulation of the first trigger assembly.

In a non-limiting exemplary embodiment, articulation of the second trigger assembly from a first position to a second position permits articulation of the first trigger assembly along a first path. Conversely, articulation of the second trigger assembly from the second position to the first position prohibits articulation of the first trigger assembly along the first path.

In a non-limiting exemplary embodiment, the ratchet arm is permitted to move in sync with the actuation arm when the second trigger assembly is displaced to the first position.

In a non-limiting exemplary embodiment, the second trigger assembly is selectively engaged to the actuation arm.

In a non-limiting exemplary embodiment, the first trigger assembly is continuously engaged to the actuation arm.

The present disclosure further includes a method of utilizing a multi-functional handle for manipulating a medical instrument. Such a method includes the steps of: providing a body having a centrally-registered longitudinal plane and capable of being gripped by a hand of a user; providing and communicating a first trigger assembly with the body wherein the first trigger assembly includes an actuation arm and a primary digit-receiving member in communication with the actuation arm; selectively displacing the actuation arm at alternate positions generally coplanar with the centrally-registered longitudinal plane of the body such that the actuation arm actuates the medical instrument independently from movement of the primary digit-receiving member; and selectively displacing the primary digit-receiving member between alternate orientations relative to a position of the body and relative to a position of the actuation arm, respectively.

There has thus been outlined, rather broadly, the more important features of non-limiting exemplary embodiment(s) of the present disclosure so that the following detailed description may be better understood, and that the present contribution to the relevant art(s) may be better appreciated. There are additional features of the non-limiting exemplary embodiment(s) of the present disclosure that will be described hereinafter and which will form the subject matter of the claims appended hereto.

BRIEF DESCRIPTION OF THE NON-LIMITING EXEMPLARY DRAWINGS

The novel features believed to be characteristic of non-limiting exemplary embodiment(s) of the present disclosure are set forth with particularity in the appended claims. The non-limiting exemplary embodiment(s) of the present disclosure itself, however, both as to its organization and method of operation, together with further objects and advantages thereof, may best be understood by reference to the following description taken in connection with the accompanying drawings in which:

FIG. 2 is a partially exposed side elevational view illustrating the interrelationship between the internal components of the multi-functional handle shown in FIG. 1;

FIG. 3 is an enlarged view of the second trigger assembly shown in FIG. 2;

FIG. 5 is an exposed view illustrating the interrelationship between the first trigger assembly, second trigger assembly and third trigger assembly;

FIG. 6 is an enlarged view of section 6, taken in FIG. 5, illustrating the interrelationship between the first trigger assembly, second trigger assembly and third trigger assembly;

FIG. 8 is an enlarged perspective view illustrating the interrelationship between the major internal components of the third digit assembly;

FIG. 9 is an enlarged perspective view illustrating a receiving aperture of the digit-receiving member;

FIG. 10 is an exploded view illustrating a non-limiting exemplary embodiment of the first and third trigger assemblies shown in FIG. 1;

FIG. 10A is a perspective view of the first and third trigger assemblies illustrated in FIG. 10, wherein the digit-receiving member is oriented at an aligned position;

FIG. 10B is a perspective view of the first and third trigger assemblies illustrated in FIG. 10, wherein the digit-receiving member is oriented at an angularly offset position;

FIG. 11 is an exploded view illustrating an alternate embodiment of the first and third trigger assemblies wherein the digit-receiving member is linearly adjustable relative to the actuation arm;

FIG. 11A is a perspective view of the first trigger assembly illustrated in FIG. 11, wherein the digit-receiving member is oriented at a retracted position relative to the actuation arm;

FIG. 11B is a perspective view of the first trigger assembly illustrated in FIG. 11, wherein the digit-receiving member is oriented at an extended position relative to the actuation arm;

FIG. 12 is an exploded view illustrating a non-limiting exemplary embodiment of the first and third trigger assemblies;

FIG. 12A is a perspective view of the first and third trigger assemblies illustrated in FIG. 12, wherein the digit-receiving member is oriented at an aligned position (intersection of an x-axis, y-axis, and z-axis);

FIG. 12B is a perspective view of the first and third trigger assemblies illustrated in FIG. 12, wherein the digit-receiving member is angularly offset about the x-axis, y-axis, and z-axis shown in FIG. 12A;

FIG. 13 is an exploded view illustrating a non-limiting exemplary embodiment of the secondary digit-receiving member and tertiary digit-supporting member, shown in FIG. 1;

FIG. 13A is a perspective view of the digit-retaining members illustrated in FIG. 13, wherein the tertiary digit-supporting member is oriented at an equilibrium position;

FIG. 13B is a perspective view of the digit-retaining members illustrated in FIG. 13A, wherein the tertiary digit-supporting member is oriented at an angularly articulated position;

FIG. 15A is a side elevational view illustrating the lower portion angularly displaced relative to the upper portion;

FIG. 15B is a rear elevational view of the displaced lower portion illustrated in FIG. 15;

FIG. 15C is a rear elevational view of the angularly displaced lower portion illustrated in FIG. 15A;

FIG. 17 is a side elevational view illustrating a non-limiting exemplary embodiment including a bifurcated body having a lower portion displaced relative to a upper portion thereof;

FIG. 17A is a side elevational view illustrating the lower portion angularly displaced relative to the upper portion;

FIG. 17B is a rear elevational view of the displaced lower portion illustrated in FIG. 17;

FIG. 17C is a rear elevational view of the angularly displaced lower portion illustrated in FIG. 17A;

FIG. 18 is a perspective view illustrating a non-limiting exemplary embodiment including a bifurcated body having a lower portion pivotally coupled to a upper portion thereof;

FIG. 18A is a perspective view illustrating the lower portion of FIG. 18 pivotally rotated relative to the upper portion;

FIG. 21A is a side elevational view illustrating the medical instrument of FIG. 21 pivotally rotated relative to the body of the handle;

FIG. 22A is a perspective view illustrating the lower portion of FIG. 22 linearly displaced relative to the upper portion;

FIG. 23A is a perspective view illustrating the lower portion of FIG. 23 linearly displaced relative to the upper portion;

FIG. 24A is a perspective view illustrating the upper portion of FIG. 24 linearly displaced relative to the lower portion;

FIG. 25A is a perspective view illustrating the lower portion of FIG. 25 linearly displaced relative to the upper portion;

FIG. 28 is a partially exposed view of the body shown in FIG. 27 wherein portions of the second trigger assembly have been removed; and FIG. 28A is an enlarged view of the exposed portion identified in FIG. 28.

Figure 1:
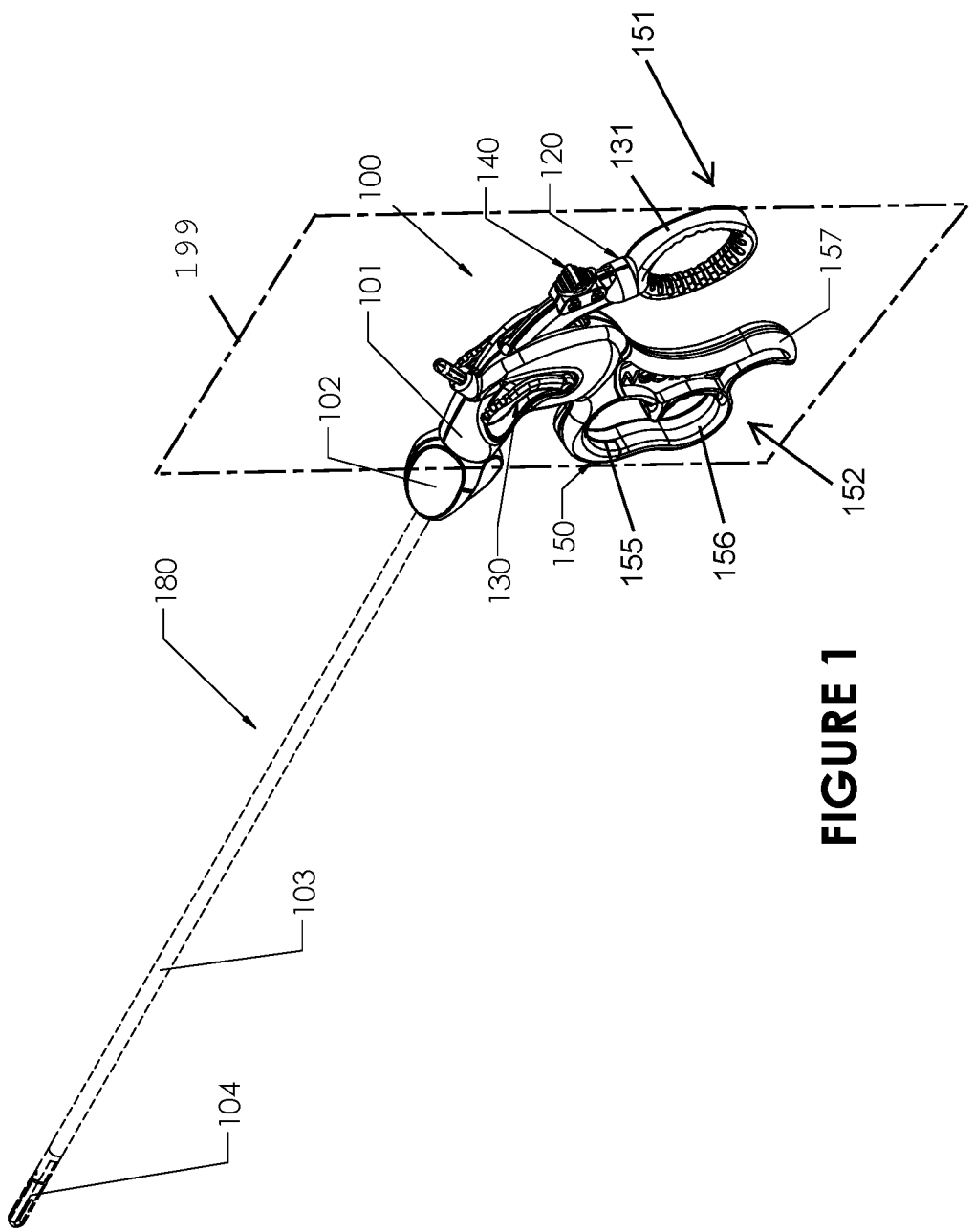
FIG. 1 is a perspective view showing a multi-functional handle for use with a medical instrument, in accordance with the non-limiting exemplary embodiment(s)

Those skilled in the art will appreciate that the figures are not intended to be drawn to any particular scale; nor are the figures intended to illustrate every non-limiting exemplary embodiment(s) of the present disclosure. The present disclosure is not limited to any particular non-limiting exemplary embodiment(s) depicted in the figures nor the shapes, relative sizes or proportions shown in the figures.

DETAILED DESCRIPTION OF NON-LIMITING EXEMPLARY EMBODIMENT(S) OF THE PRESENT DISCLOSURE

The present disclosure will now be described more fully hereinafter with reference to the accompanying drawings, in which non-limiting exemplary embodiment(s) of the present disclosure is shown. The present disclosure may, however, be embodied in many different forms and should not be construed as limited to the non-limiting exemplary embodiment(s) set forth herein. Rather, such non-limiting exemplary embodiment(s) are provided so that this application will be thorough and complete, and will fully convey the true spirit and scope of the present disclosure to those skilled in the relevant art(s). Like numbers refer to like elements throughout the figures.

The illustrations of the non-limiting exemplary embodiment(s) described herein are intended to provide a general understanding of the structure of the present disclosure. The illustrations are not intended to serve as a complete description of all of the elements and features of the structures, systems and/or methods described herein. Other non-limiting exemplary embodiment(s) may be apparent to those of ordinary skill in the relevant art(s) upon reviewing the disclosure. Other non-limiting exemplary embodiment(s) may be utilized and derived from the disclosure such that structural, logical substitutions and changes may be made without departing from the true spirit and scope of the present disclosure. Additionally, the illustrations are merely representational are to be regarded as illustrative rather than restrictive.

One or more embodiment(s) of the disclosure may be referred to herein, individually and/or collectively, by the term "non-limiting exemplary embodiment(s)" merely for convenience and without intending to voluntarily limit the true spirit and scope of this application to any particular non-limiting exemplary embodiment(s) or inventive concept. Moreover, although specific embodiment(s) have been illustrated and described herein, it should be appreciated that any subsequent arrangement designed to achieve the same or similar purpose may be substituted for the specific embodiment(s) shown. This disclosure is intended to cover any and all subsequent adaptations or variations of other embodiment(s). Combinations of the above embodiment(s), and other embodiment(s) not specifically described herein, will be apparent to those of skill in the relevant art(s) upon reviewing the description.

References in the specification to "one embodiment(s)", "an embodiment(s)", "a preferred embodiment(s)", "an alternative embodiment(s)" and similar phrases mean that a particular feature, structure, or characteristic described in connection with the embodiment(s) is included in at least an embodiment(s) of the non-limiting exemplary embodiment(s). The appearances of the phrase "non-limiting exemplary embodiment" in various places in the specification are not necessarily all meant to refer to the same embodiment(s).

Directional and/or relationary terms such as, but not limited to, left, right, nadir, apex, top, bottom, vertical, horizontal, back, front and lateral are relative to each other and are dependent on the specific orientation of an applicable element or article, and are used accordingly to aid in the description of the various embodiment(s) and are not necessarily intended to be construed as limiting.

The non-limiting exemplary embodiment(s) is/are referred to generally in FIGS. 1-28A and are intended to provide an ergonomic multi-functional handle 100 used to manipulate a medical instrument 180 such as an electrosurgical, monopolar, laparoscopic instrument, for example, while reducing user fatigue. It should be understood that such non-limiting exemplary embodiment(s) may be used to manipulate many different types of medical instruments 180, and should not be limited to the uses described herein.

Referring initially to FIG. 1, in accordance with the non-limiting exemplary embodiment(s), a perspective view showing a multi-functional handle 100 for use with a medical instrument 180 is disclosed. Such a handle 100 includes a body 150 having a plurality of digit-receiving members (primary digit-receiving member 131, secondary digit-receiving members 155, 156 and tertiary digit-supporting member 157) and a first trigger assembly 120 operatively coupled to second trigger assembly 130. A third trigger assembly 140 locks the primary digit-receiving member 131 at a desired position relative to the body 150.

The term digit, as used in the present disclosure, is intended to mean any portion(s) of a user's hand, thumb, metacarpals, phalanges, fingers, etc. The terms "first position" and "second position" mean both up and down positions relative to each other for permitting and prohibiting movement of the first trigger assembly 120. For example, the "first position" can be either the up position or down position. The "second position" can be either the up position or down position, so long as it is not the same as the "first position."

In preferred embodiments, as shown in FIGS. 1-26A, the ergonomic multi-functional handle 100 may be operated with a second trigger assembly 130 (described herein below).

Figure 27:
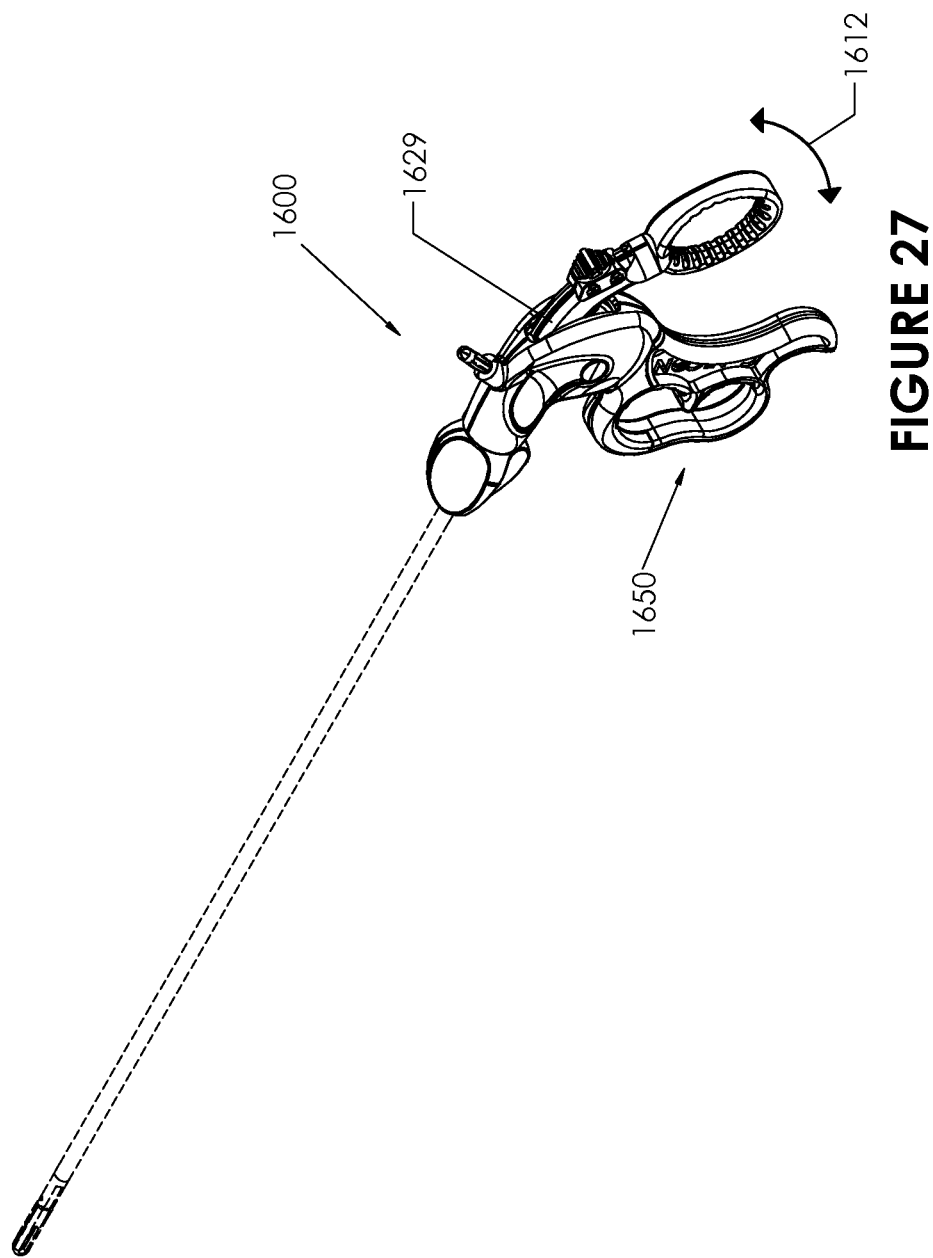
FIG. 27 is a perspective illustrating a non-limiting exemplary embodiment of the handle without use of a second triggering assembly (ratchet locking mechanism)

In a preferred embodiment, as shown in FIGS. 27-28A, the ergonomic multi-functional handle 100 may be operated without the second trigger assembly 130 (described herein below).

FIGS. 1-28A illustrate various embodiments of a multi-functional handle 100 for manipulating a medical instrument 180. Such a multi-functional handle 100 includes a body 150 capable of being gripped by a hand of a user and further capable of being in communication with a medical instrument 180 via a distal end 101 equipped with a rotation knob 102 as well as a first trigger assembly 120 (described in more detail herein below). The secondary digit-receiving members 155, 156 may include a curvilinear distal outer surface 108 having a concave radius of curvature suitable sized and shaped to receive a user digit thereagainst. Curvilinear surfaces 109, 110 may be ribbed or otherwise corrugated to receive one or more user digits. Such surfaces 108, 109, 110 may be portions of complete loops and/or incomplete loops. Body 150 includes a first portion 151 and a second portion 152 coupled thereto such that the second portion 152 is displaced relative to the first portion 151. In this manner, one of the first portion 151 and the second portion 152 is capable of manipulating the medical instrument 180. The terms "first portion" 151 and "second portion" 152 may include upper and lower portions of the body 150, which may include one or more of the primary digit-receiving member 131, secondary digit-receiving member 155, 156, and tertiary digit-supporting member 157. Also, the "first portion" 151 and/or the "second portion" 152 may be formed from deformably resilient material and/or rigid plastic.

In a non-limiting exemplary embodiment, as shown FIGS. 1-26A, the multi-functional handle 100 further includes a first trigger assembly 120. Such a first trigger assembly 120 preferably includes an actuation arm 129, and the primary digit-receiving member 131 coupled to the actuation arm 129. The first trigger assembly 120 is pivotally coupled to the body 150 in such a manner that the actuation arm 129 is capable of actuating the medical instrument 180 independently from movement of the primary digit-receiving member 131. In this manner, the primary digit-receiving member 131 is selectively displaced between alternate orientations relative to a position of the body 150 and relative to a position of the actuation arm 129, respectively.

In a non-limiting exemplary embodiment, when each of the first portion 151, second portion 152 and first trigger assembly 120 are present, both the first trigger assembly 120 as well as one of the first portion 151 and second portion 152 operates the medical instrument 180.

In a non-limiting exemplary embodiment, when each of the first portion 151, second portion 152 and first trigger assembly 120 are present, either the first trigger assembly 120 or at least one of the first portion 151 and second portion 152 operates the medical instrument 180.

In a non-limiting exemplary embodiment, the primary digit-receiving member 131 is selectively displaced between alternate orientations relative to a position of the body 150 and relative to a position of the actuation arm 129, respectively.

In a non-limiting exemplary embodiment, the multi-functional handle 100 includes a body 150 having a centrally-registered longitudinal plane 199 wherein the body 150 is capable of being gripped by an object (e.g., by a hand of a user, controller, etc.). The handle 100 further includes a first trigger assembly 120 coupled to the body 150. Such a first trigger assembly 120 includes an actuation arm 129 and a primary digit-receiving member 131 in communication with the actuation arm 129. The primary digit-receiving member 131 is selectively displaced between alternate orientations relative to a position of the body 150 and relative to a position of the actuation arm 129, respectively. In this manner, the actuation arm 129 is capable of actuating the medical instrument 180 independently from movement of the primary digit-receiving member 131.

In a non-limiting exemplary embodiment, the handle 100 further includes a second trigger assembly 130 operatively coupled to the first trigger assembly 120 in such a manner that the actuation arm 129 is selectively displaced at alternate positions generally coplanar with the centrally-registered longitudinal plane 199 of the body 150.

In a non-limiting exemplary embodiment, the first trigger assembly 120 is pivotal about a first pivot axis 126 wherein the second trigger assembly 130 is pivotal about a second pivot axis 127 wherein each of the first and second pivot axes 126, 127 are offset and traverse the centrally-registered longitudinal plane 199 of the body 150.

In a non-limiting exemplary embodiment, the primary digit-receiving member 131 is adjustably positioned about a proximal end of the actuation arm 129.

In a non-limiting exemplary embodiment, the actuation arm 129 is displaced along a first path 112 generally coplanar with the centrally-registered longitudinal plane 199 of the body 150.

In a non-limiting exemplary embodiment, the primary digit-receiving member 131 is simultaneously displaced relative to the actuation arm 129 while the first trigger assembly 120 is articulated about the first pivot axis 126.

In a non-limiting exemplary embodiment, the primary digit-receiving member 131 is a loop capable of receiving a digit of the user while the user grasps the body 150.

In a non-limiting exemplary embodiment, the primary digit-receiving member 131 is an incomplete loop capable of receiving a digit of the user while the user grasps the body 150.

In a non-limiting exemplary embodiment, the primary digit-receiving member 131 has a linear shape capable of supporting a digit of the user while the user grasps the body 150, and while the actuation arm 129 is articulated along a first path 112.

In a non-limiting exemplary embodiment, the primary digit-receiving member 131 is registered parallel to the centrally-registered longitudinal plane 199 of the body 150.

In a non-limiting exemplary embodiment, the primary digit-receiving member 131 is registered oblique to the centrally-registered longitudinal plane 199 of the body 150.

In a non-limiting exemplary embodiment, the primary digit-receiving member 131 is registered orthogonal to the centrally-registered longitudinal plane 199 of the body 150.

In a non-limiting exemplary embodiment, the actuation arm 129 includes a ratchet arm 153 statically connected thereto.

In a non-limiting exemplary embodiment, the ratchet arm 153 is monolithically formed with the actuation arm 129.

In a non-limiting exemplary embodiment, the ratchet arm 153 is coplanar with the centrally-registered longitudinal plane 199 of the body 150.

In a non-limiting exemplary embodiment, the ratchet arm 153 is integrally mated to the actuation arm 129.

In a non-limiting exemplary embodiment, the ratchet arm 153 remains fixedly coupled to the actuation arm 129 during articulation of the first trigger assembly 120.

Figure 4:
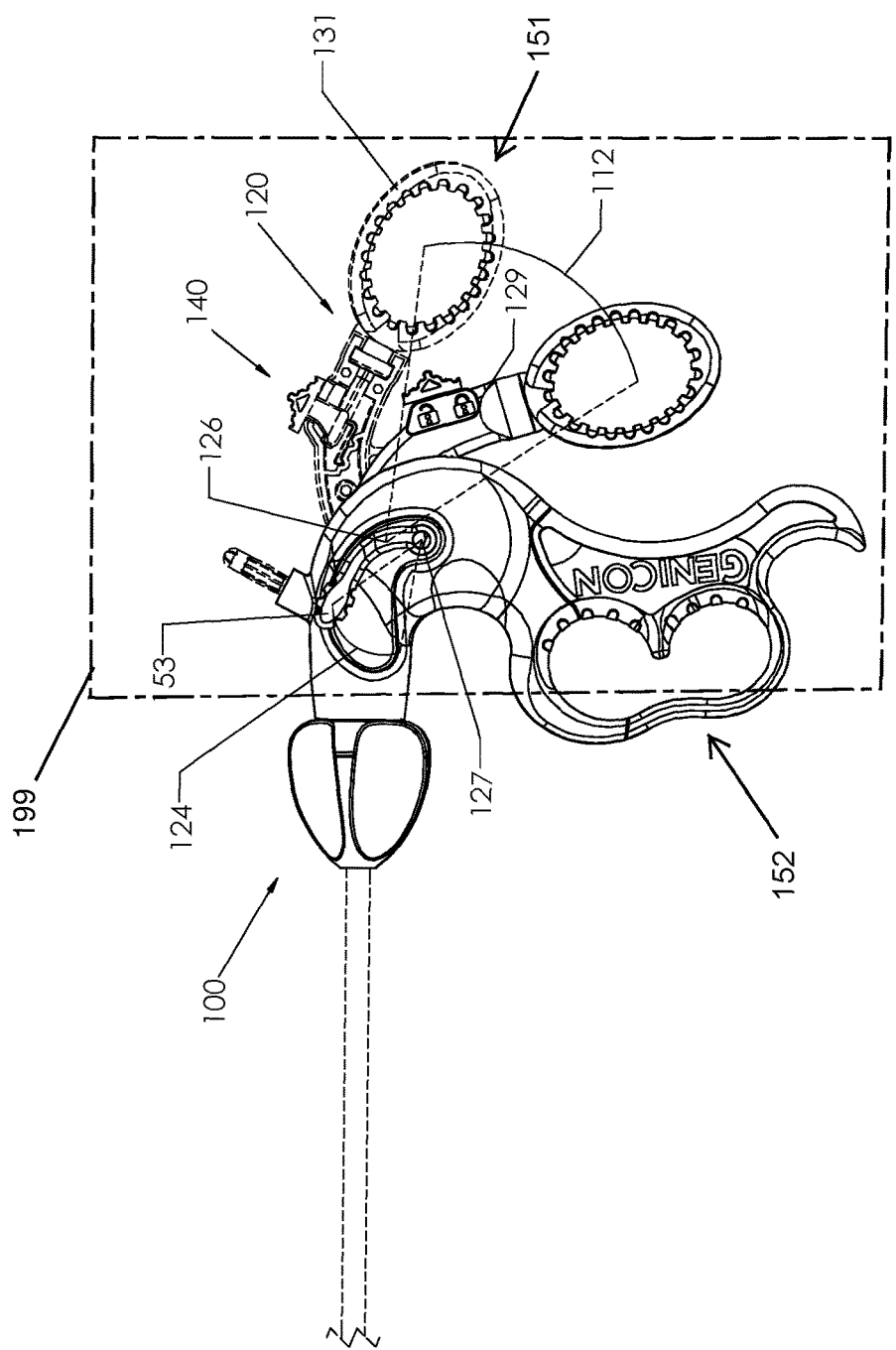
FIG. 4 is an enlarged side elevational view illustrating articulation of a first trigger assembly about a first pivot axis, and articulation of the second trigger assembly about a second pivot axis.
Figure 7:
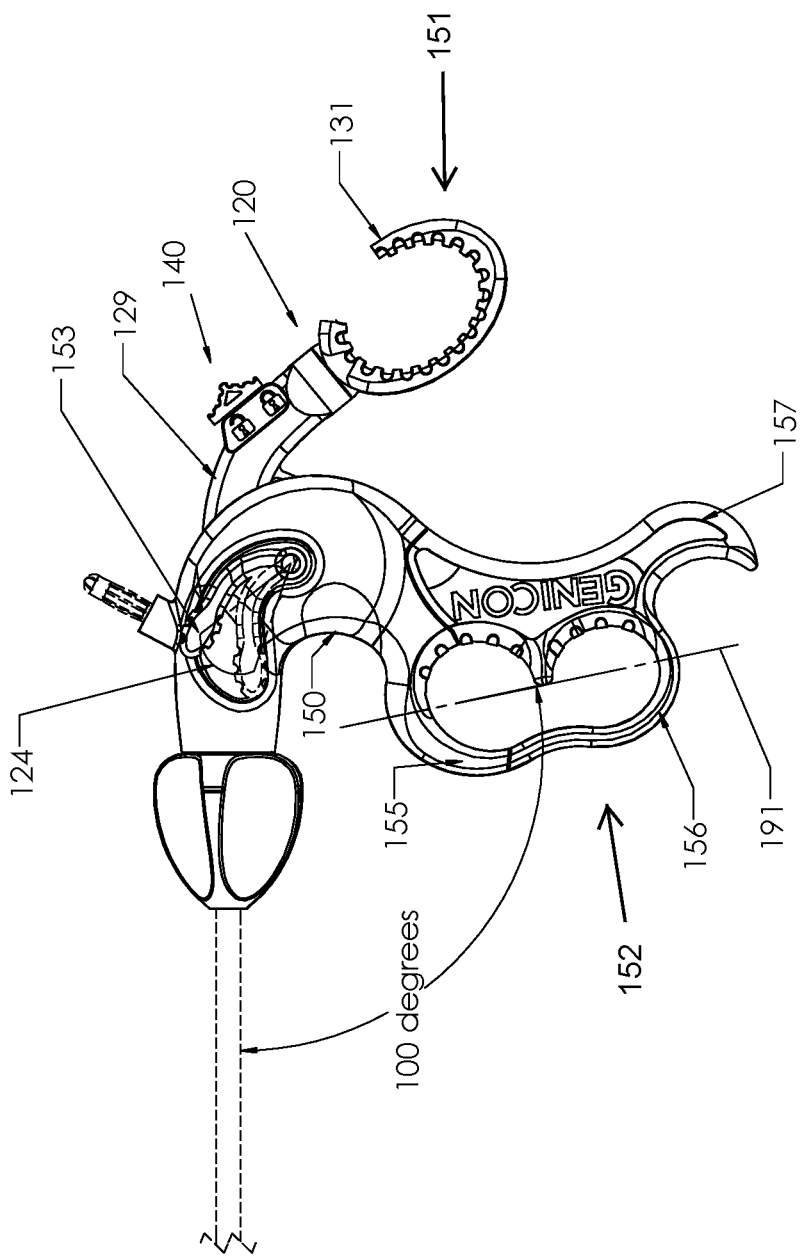
FIG. 7 is an enlarged side elevational view illustrating articulation of the second trigger assembly about the second pivot axis and articulation of the medical instrument along an arcuate path proximate to said body.

In a non-limiting exemplary embodiment, as perhaps best shown in FIGS. 4 and 7, articulation of the second trigger assembly 130 from a first position (e.g., up/down) to a second position (e.g., up/down) permits articulation of the first trigger assembly 120 along a first path 112. Conversely, articulation of the second trigger assembly 130 from the second position to the first position prohibits articulation of the first trigger assembly 120 along the first path 112.

In a non-limiting exemplary embodiment, the ratchet arm 153 is permitted to move in sync with the actuation arm 129 when the second trigger assembly 130 is displaced to the first position (e.g., up/down).

In a non-limiting exemplary embodiment, the second trigger assembly 130 is selectively engaged to the actuation arm 129.

In a non-limiting exemplary embodiment, the first trigger assembly 120 is continuously engaged to the actuation arm 129.

The present disclosure further includes a method of utilizing a multi-functional handle 100 for manipulating a medical instrument 180. Such a method includes the steps of: providing a body 150 having a centrally-registered longitudinal plane 199 and capable of being gripped by a hand of a user; providing and communicating a first trigger assembly 120 with the body 150 wherein the first trigger assembly 120 includes an actuation arm 129 and a primary digit-receiving member 131 in communication with the actuation arm 129; selectively displacing the actuation arm 129 at alternate positions generally coplanar with the centrally-registered longitudinal plane 199 of the body 150 such that the actuation arm 129 actuates the medical instrument 180 independently from movement of the primary digit-receiving member 131; and selectively displacing the primary digit-receiving member 131 between alternate orientations relative to a position of the body 150 and relative to a position of the actuation arm 129, respectively.

Figure 14:
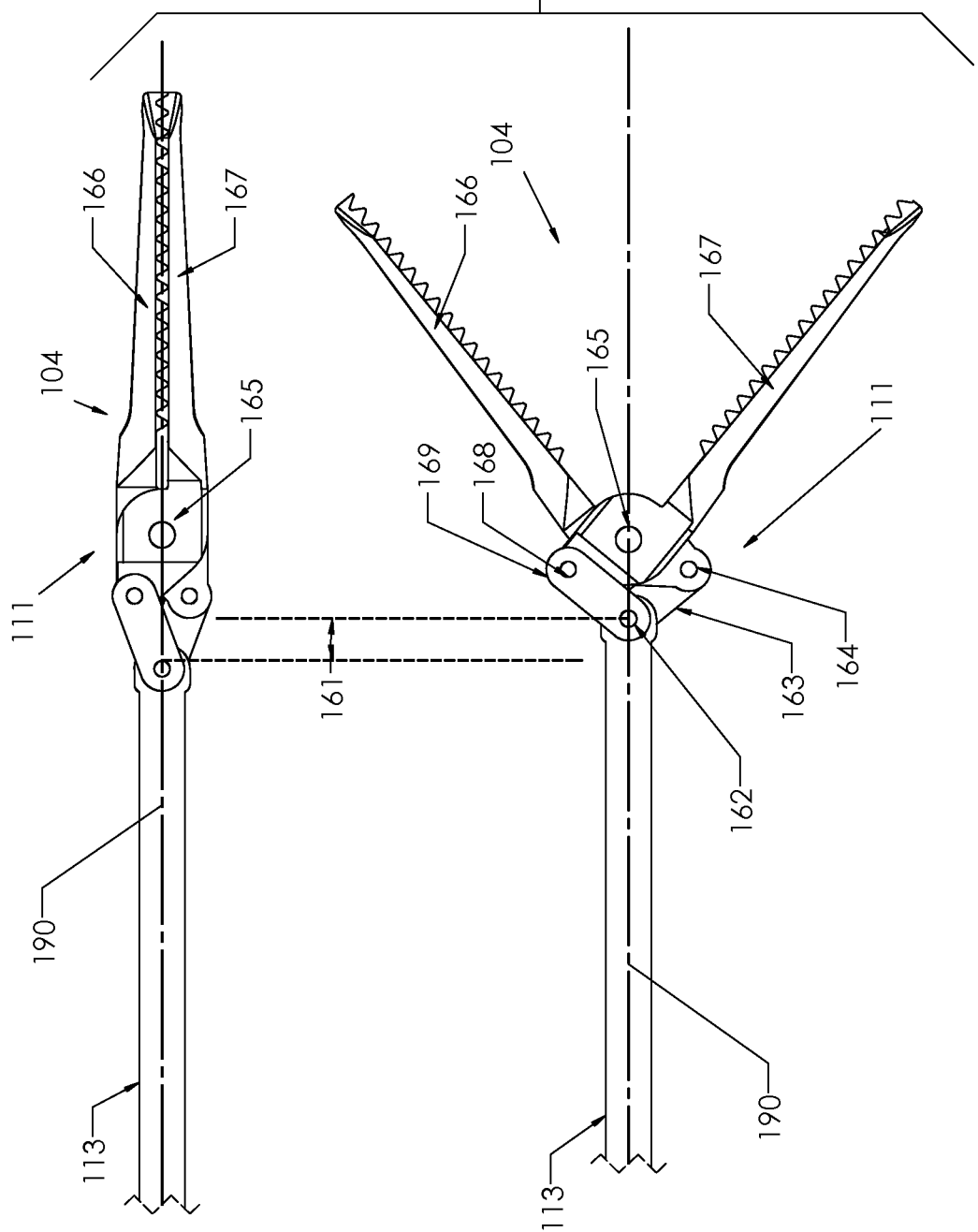
FIG. 14 is are enlarged side elevational views showing articulation of the medical instrument between open and closed positions.

In a non-limiting exemplary embodiment, as perhaps best shown in FIGS. 1 and 14, the first trigger assembly 120 is operatively coupled to the medical instrument 180 (e.g., laparoscopic tool 180). The medical instrument 180 includes a rectilinear drive rod 113 having a proximal end operatively coupled to the handle 100, as will be explained in more detail hereinbelow. A distal end of the drive rod 113 contains a linkage assembly 111 operatively coupled to a conventional jaw assembly 104. One skilled in the art understands the conventional operation of such components. The linkage assembly 111 includes a first link lever 163 and a second link lever 169 pivotally coupled to opposite sides of the distal end of the drive rod 113. Manipulation of the drive rod 113—via first trigger assembly 120—causes articulated of the first and second link levers 163, 169 about a common fulcrum axis 162 at the distal end of the drive rod 113. Such first and second link levers 163, 169 are also pivotally coupled to first jaw 166 and second jaw 167, at joints 164, 168, respectively. First and second jaws 166, 167 are pivotally coupled to each other via a jaw pin 165. In this manner, when the distal end of the drive rod 113 is linearly urged—along distance 161—towards the first and second jaws 166, 167, the first and second link levers 163, 169 are caused to pivot along first rotational directions, away from a longitudinal axis 190 of the drive rod 113. Such pivotal movement urges apart the first and second jaws 166, 167 to an open position. Retraction of the drive rod 113—along distance 161—away from the jaw pin 165 causes the first and second link levers 163, 169 to articulate towards the longitudinal axis 190 of the drive rod 113 and thereby articulate the first and second jaws 166, 167 towards a closed position.

Referring to FIG. 2, in a non-limiting exemplary embodiment, a partially exposed side elevational view illustrating the interrelationship between the internal components of the multi-functional handle 100 shown in FIG. 1, is disclosed. The first trigger assembly 120 operates the medical instrument 180 wherein the rectilinear drive rod 113 is housed within the shaft 103. A proximal end of the drive rod 113 is attached to a distal end of the actuation arm 129. Such a drive rod 113 may be connected to the actuation arm 129 via a ball/socket joint 128, 142 or other fastener suitable for reciprocating the drive rod 113 along a linear travel path 161 defined parallel to the longitudinal axis 190 of the shaft 103 (as perhaps best shown in FIG. 14). FIGS. 6 and 8 illustrate the drive rod ball joint 128 and actuation arm 129 ball socket 142. Articulation of the first trigger assembly 120 is effectuated by manual manipulation of the actuation arm 129 along the arcuate path illustrated by the arrow 112. Connection between the actuation arm 129 and drive rod 113 is spaced from the first pivot axis 126 about which the first trigger assembly 120 pivots. A rotation knob joint 105 is attached to the drive rod 113 at a distal location of the body 150 so that the medical instrument 180 can be selectively articulated via rotation of the actuation arm 129 at a proximal end of the body 150. Of course, alternately, the position of the actuation arm 129 may be located at a distal end of body 150.

Referring to FIG. 2, in a non-limiting exemplary embodiment, an electrical current may be supplied to the medical instrument 180 via a high-frequency (HF) connector plug 107 extending outwardly and away from a top of the body 150. A HF connector lead 106 is communicatively coupled to the connector plug 107 and travels downward into a hollow cavity of the body 150 wherein it maintains electrical communication with the drive rod 113.

In a non-limiting exemplary embodiment, an energy source such as a tissue-altering energy source may be communicatively coupled to the handle 100. Exemplary tissue-altering energy sources may generate a heat signal, acoustic signal, microwave signal, light signal, etc., as well-understood by one of ordinary skill in the art. Each tissue-altering energy source may include different components for interfacing with the body 150 and/or the medical instrument 180. Thus, the HF connector plug 107 and lead 106 are not a necessity and are merely provided as an illustrative example; not restrictive.

Referring to FIG. 3, in a non-limiting exemplary embodiment, an enlarged view of the second trigger assembly 130, taken in FIG. 2, is disclosed. As noted above, the second trigger assembly 130 permits selective articulation of a portion—actuation arm 129—of the first trigger assembly 120 along the arcuate path 112 for manipulating the medical instrument 180 (e.g., jaws). Of course, one skilled in the art understands a variety of medical instruments 180 may be manipulated by movement of the first trigger assembly 120.

In a non-limiting exemplary embodiment, the second trigger assembly 130 is employed to selectively lock the actuation arm 129 at alternate positions, as desired. Thus, while the first trigger assembly 120 permits operation of the medical instrument 180, the second trigger assembly 130 enables the user to lock the first trigger assembly 120 at a desired position thereby preventing further manipulation of the medical instrument 180.

In a non-limiting exemplary embodiment, as perhaps best shown in FIGS. 3, 4 and 7, the second trigger assembly 130 preferably includes a ratchet cam shaft 119 formed at the second pivot axis 127. A ratchet trigger 153 is statically coupled to the ratchet cam shaft 119 and is disposed exterior of the body 150. The ratchet trigger 153 pivots about the second pivot axis 127 thereby causing a ratchet cam shaft arm 116 to articulate in a corresponding direction. For example, when the ratchet trigger 153 is rotated clockwise, the ratchet cam shaft arm 116 also rotates clockwise; and visa-versa.

In a non-limiting exemplary embodiment, a ratchet cam shaft snap fit 117 is formed at an end of the ratchet cam shaft arm 116 and locks to a snap fit anchor bracket 117 statically housed within the body 150. For example, the snap fit anchor bracket 117 may be friction locked, magnetically locked, or locked via other suitably ways, without departing from the true spirit and scope of the present disclosure. A ratchet pawl cam 121 is statically mated to the ratchet cam shaft 119 and remains angled away from the ratchet cam shaft arm 116 such that it selectively displaces one end of a ratchet pawl 122. The ratchet pawl 122 has an opposite end anchored to a ratchet pawl attachment boss 123 located distally of the first pivot axis 126. In this manner, articulation of ratchet trigger 153 along a first rotational direction causes ratchet pawl cam 121 to urge ratchet pawl 122 towards a ratchet arm 147 having a serrated surface. A proximal end of the ratchet pawl 122 engages the ratchet arm 147 teeth 118 and the ratchet cam shaft snap fit 117 locks the ratchet trigger 153 at a locked position. Such cooperation between the ratchet pawl 122, ratchet arm 147 and ratchet cam snap fit 117 prohibit premature or undesirable movement of the ratchet trigger 153, thereby maintaining the medical instrument 180 at a desired orientation.

In a non-limiting exemplary embodiment, rotation of ratchet trigger 153 in an opposite direction releases the ratchet cam snap fit 117 and disengages the ratchet pawl 122 from the ratchet arm 147. Such disengagement permits the ratchet arm 147 to articulate in sync with the actuation arm 129 of the first trigger assembly 120 thereby permitting manipulation of the medical instrument 180 as desired.

In a non-limiting exemplary embodiment, FIG. 4 illustrates an enlarged side elevational view of the multi-functional handle 100 for articulation of the first trigger assembly 120 about the first pivot axis 126. During manipulation of the medical instrument 180, the first trigger assembly 120 articulates about the first pivot axis 126 and along a first arcuate path 112 while the ratchet trigger 153 is at a lowered position (e.g., unlocked position). To prohibit manipulation of the medical instrument 180, the ratchet trigger 153 articulates along a second arcuate travel path 124, and about a second pivot axis 127 offset from the first pivot axis 126. When the ratchet trigger 153 is articulated to a raised position (e.g., locked position), the actuation arm 129 is prohibited from rotating along the arcuate path 112. As noted herein above, raised/lowered positions maybe first/second positions and visa-versa.

In a non-limiting exemplary embodiment, FIGS. 5 and 6 are cross-sectional views showing the interrelationship between the first trigger assembly 120, second trigger assembly 130 and third trigger assembly 140. FIG. 8 is an enlarged perspective view illustrating the interrelationship between the third trigger assembly 140 and the actuation arm 129. FIG. 9 is an enlarged perspective view illustrating the receiving aperture 146 of the primary digit-receiving member 131. With reference to FIGS. 5-6 and 8-9, the digit locking switch is referred to as the third trigger assembly 140. Such a mechanism permits selective movement of the primary digit-receiving member 131, which may be a loop, for example. Of course, the primary digit-receiving member 131 may be a variety of shapes and should not be construed as limited to only a loop shape.

In a non-limiting exemplary embodiment, the third trigger assembly 140 is operably coupled to the actuation arm 129 and primary digit-receiving member 131 of the first trigger assembly 120. The third trigger assembly 140 includes a switch 149 that is linearly reciprocated along a slot 145 formed in the actuation arm 129. The switch 149 is partially inserted into the actuation arm 129 and has a switch follower 133 statically mated thereto. A switch snap fit arm 134 extends downwardly and distally from the switch follower 133, traveling along a path 141 aligned substantially parallel to the reciprocating motion of the switch 149 above. A switch snap fit 135 is formed at a distal end of switch arm 134. Grooves 137, 138 are formed within an interior wall of the actuation arm 129. Such grooves 137, 138 are aligned substantially parallel to the linear path 141 wherein, when the switch snap fit 135 is positioned in a proximal groove 137, the switch arm 134 is locked and prohibited from movement. When the switch snap fit 135 is slidably inserted in the distal groove 138, a locking shaft 132 is displaced outwardly from a receiving aperture 146 thereby permitting movement of the primary digit-receiving member 131. Although, the locking shaft 132 has a hexagonal shape with a corresponding hexagonally shaped receiving aperture 146, any number of interlocking shapes may be used to prohibit movement of primary digit-receiving member 131. The primary digit-receiving member 131 is coupled to the actuation arm 129 via a joint for maintaining the receiving aperture 146 within the actuation arm 129 during movement of the primary digit-receiving member 131; prevents primary digit-receiving member 131 from disengaging the locking shaft 132.

In a non-limiting exemplary embodiment, with reference to FIGS. 4 and 7, an enlarged perspective view illustrating articulation of the ratchet arm 153 about the second pivot axis 127 is disclosed. Also, a reference line 191 is shown passing through the secondary digit-receiving members 155, 156 located along a medial portion of the body 150. Such illustration in FIG. 7 shows an optional movement of the medical instrument 180 along approximately a 100 degree arcuate path. See also FIGS. 21 and 21A for further illustration of the medical instrument 180 movement relative to the medial portion of the body 150.

In a non-limiting exemplary embodiment, FIG. 10 is an exploded view of the third trigger assembly 140 (e.g., locking switch) communicatively coupled to the primary digit-receiving member 131—of the first trigger assembly 120—shown in FIG. 1. FIG. 10A is a perspective view of the third trigger assembly 140 illustrated in FIG. 10, wherein the primary digit-receiving member 131 is oriented at an aligned position. FIG. 10B is a perspective view of the third trigger assembly 140 illustrated in FIG. 10, wherein the primary digit-receiving member 131 is oriented at an angularly offset position. While FIG. 10B illustrates partial articulation of the primary digit-receiving member 131, it is understood that the primary digit-receiving member 131 can be articulated along 360 degree clockwise and counter clockwise paths defined about longitudinal axis 192 passing through the actuation arm 129.

FIG. 11 is an exploded view illustrating a non-limiting exemplary embodiment of a linearly adjustable primary digit-receiving member 231 (e.g., along linearly reciprocating path 295 extending from actuation arm 229). FIG. 11A is a perspective view of the first trigger assembly 220 illustrated in FIG. 11, wherein the primary digit-receiving member 231 is oriented at a retracted position. FIG. 11B is a perspective view of the first trigger assembly 220 illustrated in FIG. 11, wherein the primary digit-receiving member 231 is oriented at an extended position. The third trigger assembly 240 may include a detent or other fastener to frictionally engage a tab 241 with a plurality of indentations 242 formed along a neck of the primary digit-receiving member 231.

FIG. 12 is an exploded view illustrating a non-limiting exemplary embodiment of an angularly adjustable primary digit-receiving member 331. FIG. 12A is a perspective view of the first trigger assembly 320 illustrated in FIG. 12, wherein the primary digit-receiving member 331 is oriented at a longitudinally aligned position. FIG. 12B is a perspective view of the first trigger assembly 320 illustrated in FIG. 12, wherein the primary digit-receiving member 331 is oriented at an angularly offset position. Thus, the third trigger assembly 340 may include a ball/socket joint 341. While FIG. 12B illustrates partial articulation of the primary digit-receiving member 331, it is understood that the primary digit-receiving member 331 can be articulated about x, y and z axes (e.g., ball/socket joint 341).

FIG. 13 is an exploded view illustrating a non-limiting exemplary embodiment of tertiary digit-supporting member 1757 employed by the multi-functional handle 1700 shown in FIG. 1. FIG. 13A is a perspective view of the tertiary digit-supporting member 1757 illustrated in FIG. 13, wherein the digit-supporting member 1757 is oriented at an equilibrium position relative to the body 1750. FIG. 13B is a perspective view of the tertiary digit-supporting member 1757 illustrated in FIG. 13, wherein the tertiary digit-supporting member 1757 is oriented at an articulated offset position. While FIG. 13B illustrates partial articulation of the tertiary digit-supporting member 1757, it is understood that the tertiary digit-supporting member 1757 can be selectively articulated along clockwise and counter clockwise paths relative to the secondary digit-receiving members 1755, 1756 of body 1750. A snap fit fastener 1758 may be employed to selectively lock the tertiary digit-supporting member 1757 at desired locations.

Figure 15:
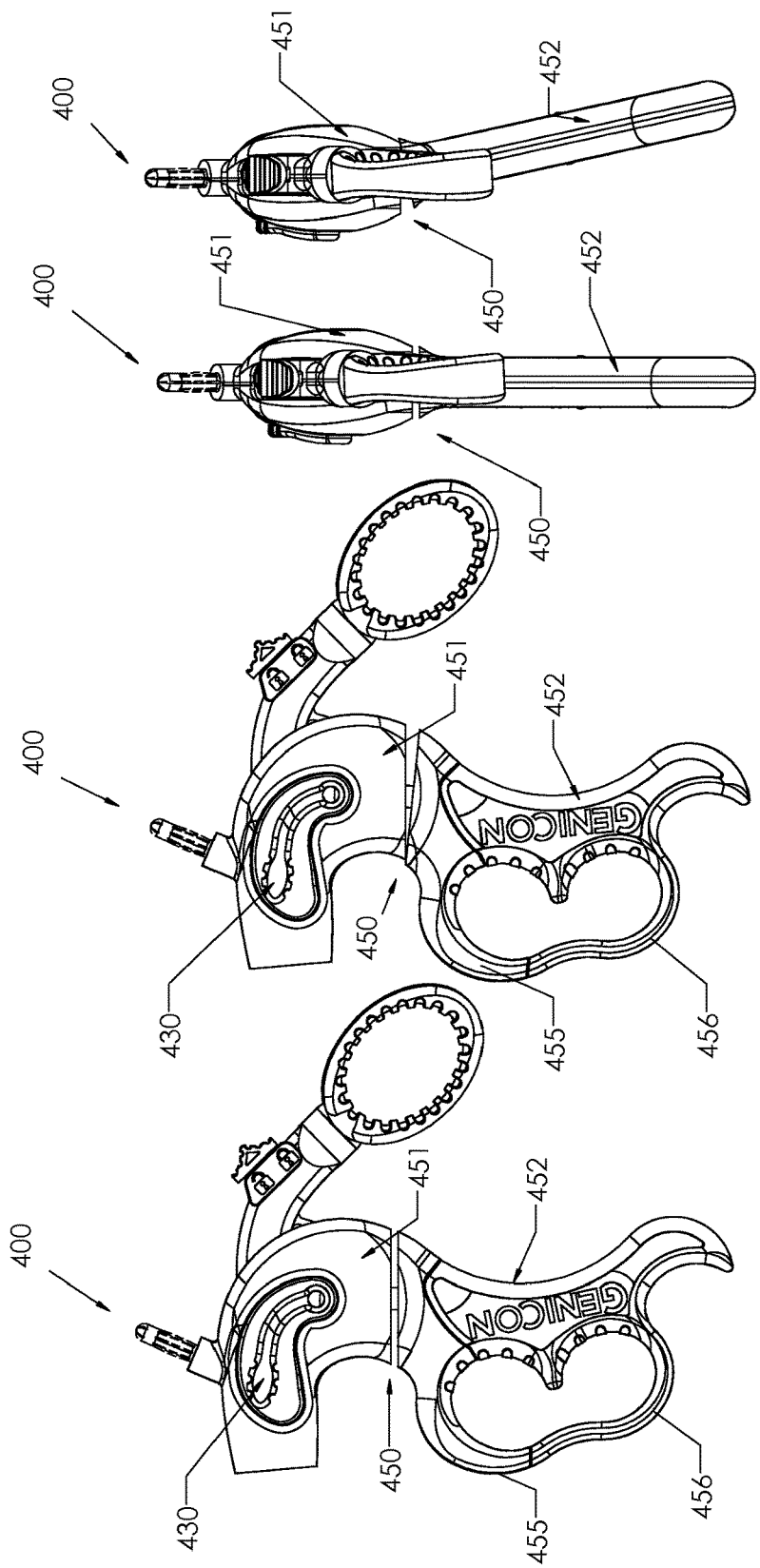
FIG. 15 is a side elevational view illustrating a non-limiting exemplary embodiment including a bifurcated body having a lower portion displaced relative to a upper portion thereof.

FIG. 15 is a side elevational view illustrating a non-limiting exemplary embodiment of the handle 400 including a bifurcated body 450 having a lower portion 452 displaced relative to an upper portion 451 thereof. FIG. 15B is a rear elevational view of the displaced lower portion 452 illustrated in FIG. 15. FIG. 15A is a side elevational view illustrating the lower portion 452 angularly displaced relative to the upper portion 451. FIG. 15C is a rear elevational view of the angularly displaced lower portion 452 illustrated in FIG. 15A. In such an embodiment, the bifurcated region of the body 450 is located intermediately of the second trigger assembly 430 and secondary digit-receiving members 455, 456. The connection between the upper portion 451 and lower portion 452 of the body 450 may be friction fitted, such as a snap-fit arrangement or via a detent, for example. A resilient coupling may also be employed for causing the lower portion 452 to automatically return to an equilibrium position from a tensioned position. It is noted that the lower portion 452 of the body 450 can be articulated about x, y and z axes (e.g., ball/socket joint). Of course, the upper portion 451 may move relative to a stationary lower portion 452 as well.

Figures 16, 16A, 16B, 16C:
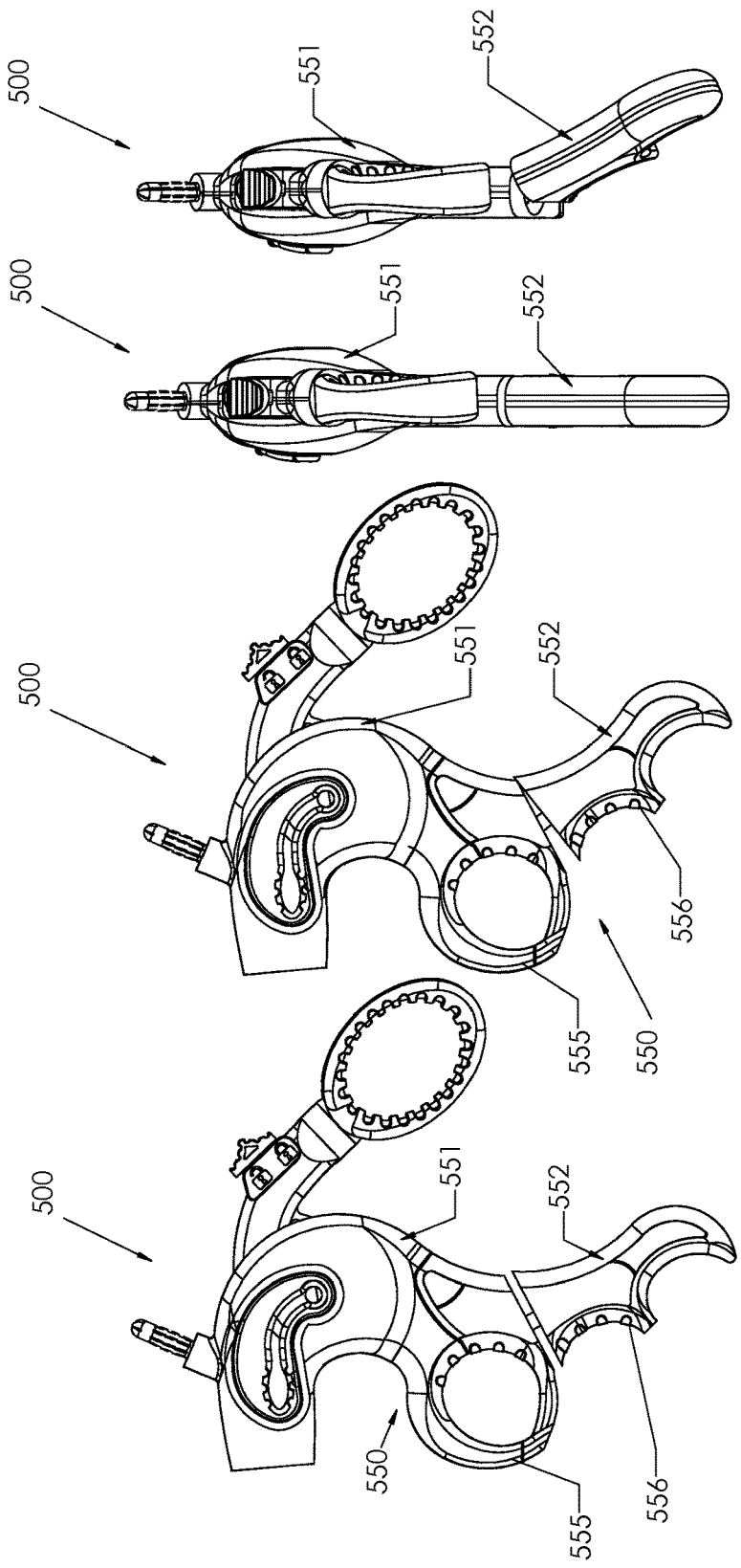
FIG. 16 is a side elevational view illustrating a non-limiting exemplary embodiment including a bifurcated body having a lower portion displaced relative to a upper portion thereof.
FIG. 16A is a side elevational view illustrating the lower portion angularly displaced relative to the upper portion.
FIG. 16B is a rear elevational view of the displaced lower portion illustrated in FIG. 16.
FIG. 16C is a rear elevational view of the angularly displaced lower portion illustrated in FIG. 16A.

FIG. 16 is a side elevational view illustrating a non-limiting exemplary embodiment of the handle 500 including a bifurcated body 550 having a lower portion 552 displaced relative to an upper portion 551 thereof. FIG. 16B is a rear elevational view of the displaced handle 500 illustrated in FIG. 16. FIG. 16A is a side elevational view illustrating the lower portion 552 angularly displaced relative to the upper portion 551. FIG. 16C is a rear elevational view of the angularly displaced lower portion 552 illustrated in FIG. 16A. In such embodiments, the bifurcated region of the body 550 separates the secondary digit-receiving members 555, 556 from each other. The connection between the upper portion 551 and lower portion 552 of the body 550 may be friction fitted, such as a snap-fit arrangement or via a detent, for example. A resilient coupling may also be employed for causing the lower portion 552 to automatically return to equilibrium from a tensioned position. It is noted that the lower portion 552 of the body 550 can be articulated about x, y and z axes (e.g., ball/socket joint). Of course, the upper portion 551 may move relative to a stationary lower portion 552 as well.

FIG. 17 is a side elevational view illustrating a non-limiting exemplary embodiment of the handle 600 including a bifurcated body 650 having a lower portion 652 displaced relative to an upper portion 651 thereof. FIG. 17B is a rear elevational view of the displaced handle 600 illustrated in FIG. 17. FIG. 17A is a side elevational view illustrating the lower portion 652 angularly displaced relative to the upper portion 651. FIG. 17C is a rear elevational view of the angularly displaced handle 600 illustrated in FIG. 17A. In such embodiments, the bifurcated region is located intermediately of the secondary digit-receiving members 655, 656 and the tertiary digit-supporting member 657. Thus, the tertiary digit-supporting member 657 is moved relative to stationary secondary digit-receiving members 655, 656. The connection between the upper portion 651 and lower portion 652 of the body 650 may be friction fitted, such as a snap-fit arrangement or via a detent, for example. A resilient coupling may also be employed for causing the lower portion 652 to automatically return to an equilibrium position from a tensioned position. It is noted that the lower portion 652 of the body 650 can be articulated about x, y and z axes (e.g., ball/socket joint). Of course, the upper portion 651 may move relative to a stationary lower portion 652 as well.

FIG. 18 is a perspective view illustrating a non-limiting exemplary embodiment of the handle 700 including a bifurcated body 750 having a lower portion 752 pivotally coupled to an upper portion 751 thereof. FIG. 18A is a perspective view illustrating the lower portion 752 of FIG. 18 angularly offset relative to the upper portion 751. In such an embodiment, the bifurcated region is located intermediately of the second trigger assembly 730 and secondary digit-receiving member 755, 756. The connection between the upper portion 751 and lower portion 752 of the body 750 may be friction fitted, such as a snap-fit arrangement or via a detent, for example. A resilient coupling may also be employed for causing the lower portion 752 to automatically return to an equilibrium position from a tensioned position. It is noted that the lower portion 752 of the body 750 can be articulated about x, y and z axes (e.g., ball/socket joint). Of course, the upper portion 751 may move relative to a stationary lower portion 752 as well.

Figure 19A:
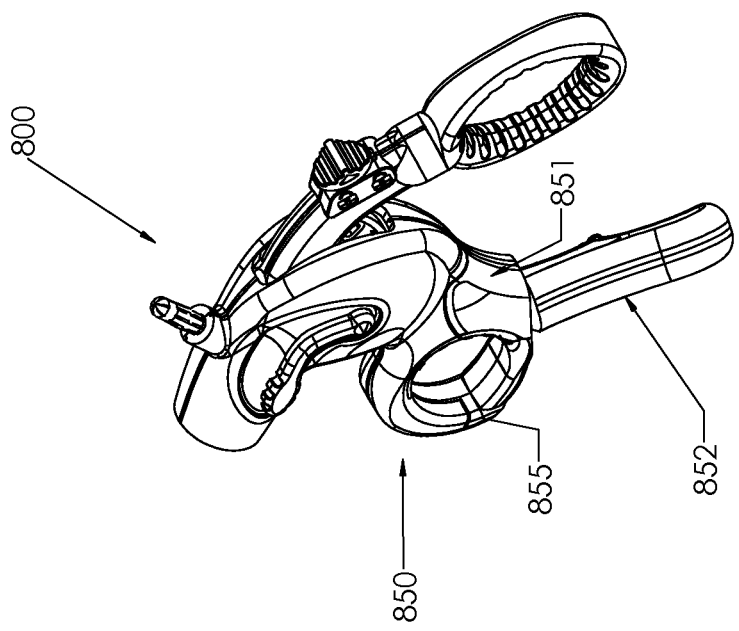
FIG. 19A is a perspective view illustrating the lower portion of FIG. 19 pivotally rotated relative to the upper portion.
Figure 19:
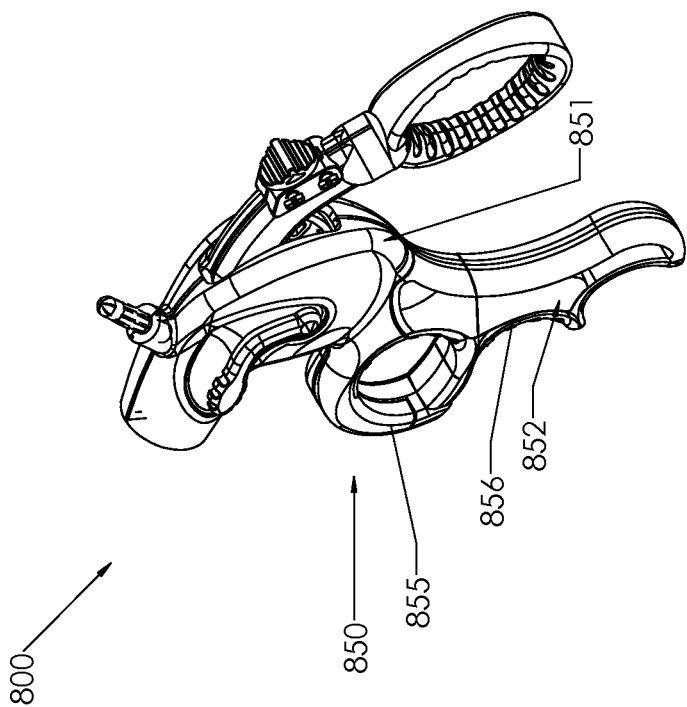
FIG. 19 is a perspective view illustrating a non-limiting exemplary embodiment including a bifurcated body having a lower portion pivotally coupled to a upper portion thereof.

FIG. 19 is a perspective view illustrating a non-limiting exemplary embodiment of the handle 800 including a bifurcated body 850 having a lower portion 852 pivotally coupled to a upper portion 851 thereof. FIG. 19A is a perspective view illustrating the lower portion 852 of FIG. 19 angularly offset relative to the upper portion 851. In such an embodiment, the bifurcated region separates the secondary digit-receiving members 855, 856 from each other. The connection between the upper portion 851 and lower portion 852 of the body 850 may be friction fitted, such as a snap-fit arrangement or via a detent, for example. A resilient coupling may also be employed for causing the lower portion 852 to automatically return to an equilibrium position from a tensioned position. It is noted that the lower portion 852 of the body 850 can be articulated about x, y and z axes (e.g., ball/socket joint). Of course, the upper portion 851 may move relative to a stationary lower portion 852 as well.

Figure 20A:
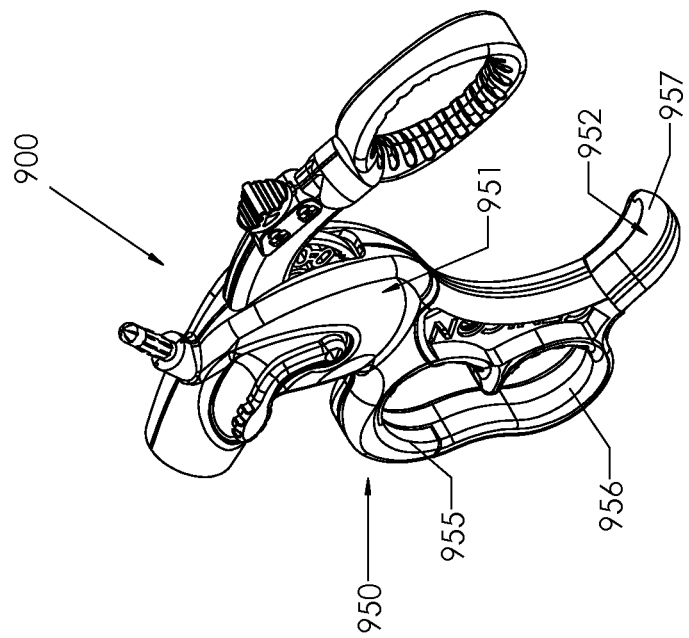
FIG. 20A is a perspective view illustrating the lower portion of FIG. 20 pivotally rotated relative to the upper portion.
Figure 20:
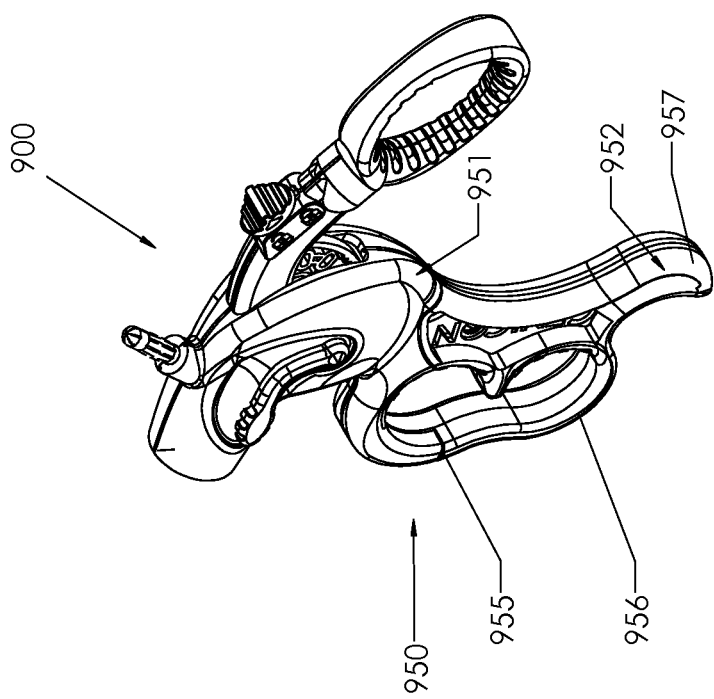
FIG. 20 is a perspective view illustrating a non-limiting exemplary embodiment including a bifurcated body having a lower portion pivotally coupled to a upper portion thereof.

FIG. 20 is a perspective view illustrating a non-limiting exemplary embodiment of the handle 900 including a bifurcated body 950 having a lower portion 952 pivotally coupled to an upper portion 951 thereof. FIG. 20A is a perspective view illustrating the lower portion 952 of FIG. 20 angularly offset relative to the upper portion 951. In such an embodiment, the bifurcated region is located intermediately of the secondary digit-receiving members 955, 956 and the tertiary digit-supporting member 957. The connection between the upper portion 951 and lower portion 952 of the body 950 may be friction fitted, such as a snap-fit arrangement or via a detent, for example. A resilient coupling may also be employed for causing the lower portion 952 to automatically return to an equilibrium position from a tensioned position. It is noted that the lower portion 952 of the body 950 can be articulated about x, y and z axes (e.g., ball/socket joint). Of course, the upper portion 951 may move relative to a stationary lower portion 952 as well.

Figure 21:
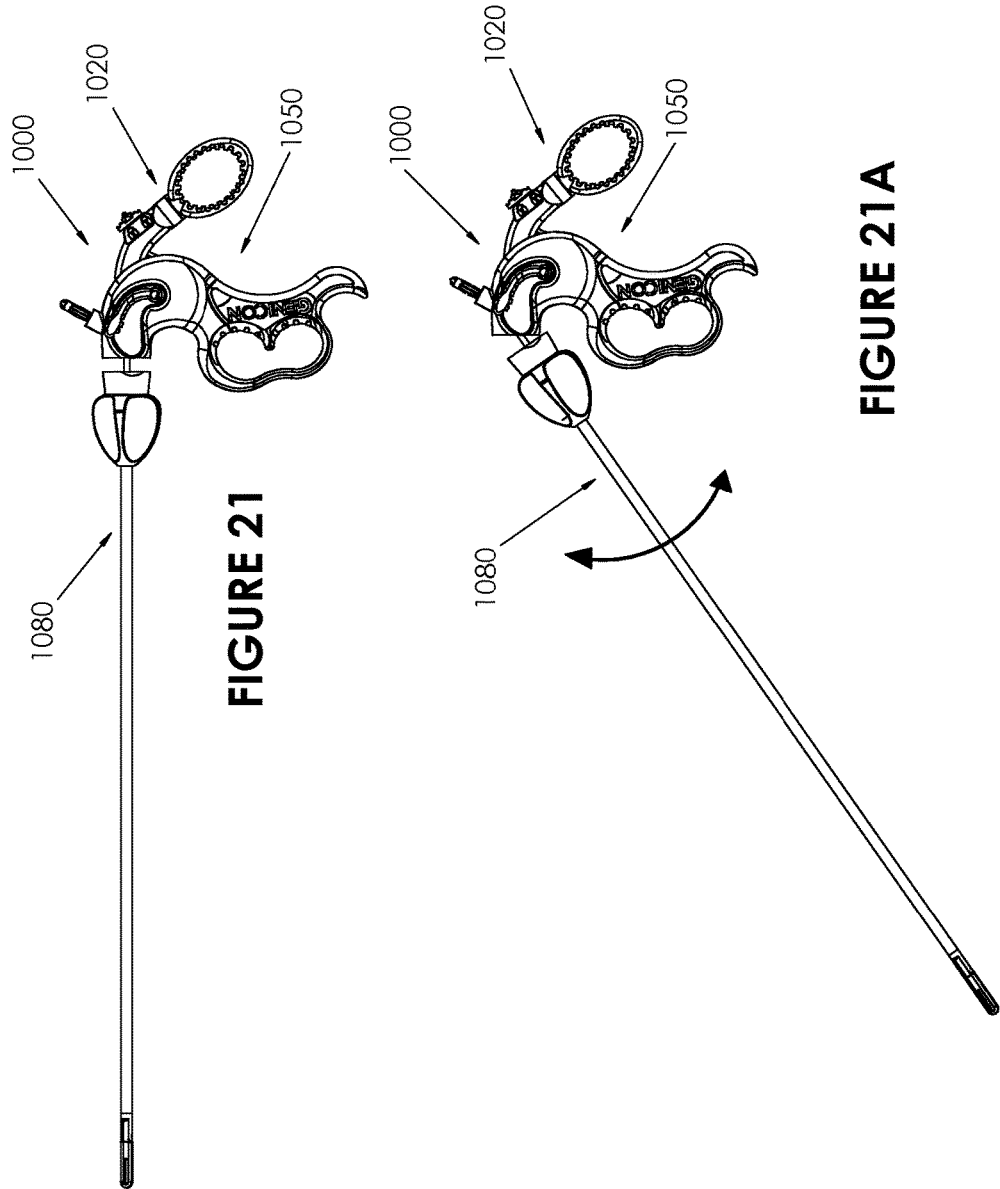
FIG. 21 is a side elevational view illustrating a non-limiting exemplary embodiment including a medical instrument pivotally coupled to the body of the handle.

FIG. 21 is a side elevational view illustrating a non-limiting exemplary embodiment including a medical instrument 1080 pivotally coupled to the body 1050 of the handle 1000. FIG. 21A is a side elevational view illustrating the medical instrument 1080 of FIG. 21 angularly offset relative to the body 1050 of the handle 1000. In such an embodiment, the bifurcated region is located between a proximal end of the medical instrument 1080 and the first trigger assembly 1020. The connection between the medical instrument 1080 and first trigger assembly 1020 may be friction fitted, such as a snap-fit arrangement or via a detent, for example. A resilient coupling may also be employed for causing the medical instrument 1080 to automatically return to an equilibrium position from a tensioned position. It is noted that the medical instrument 1080 can be articulated about x, y and z axes (e.g., ball/socket joint). Of course, the handle 1000 may move relative to a stationary medical instrument 1080 as well.

Figure 22:
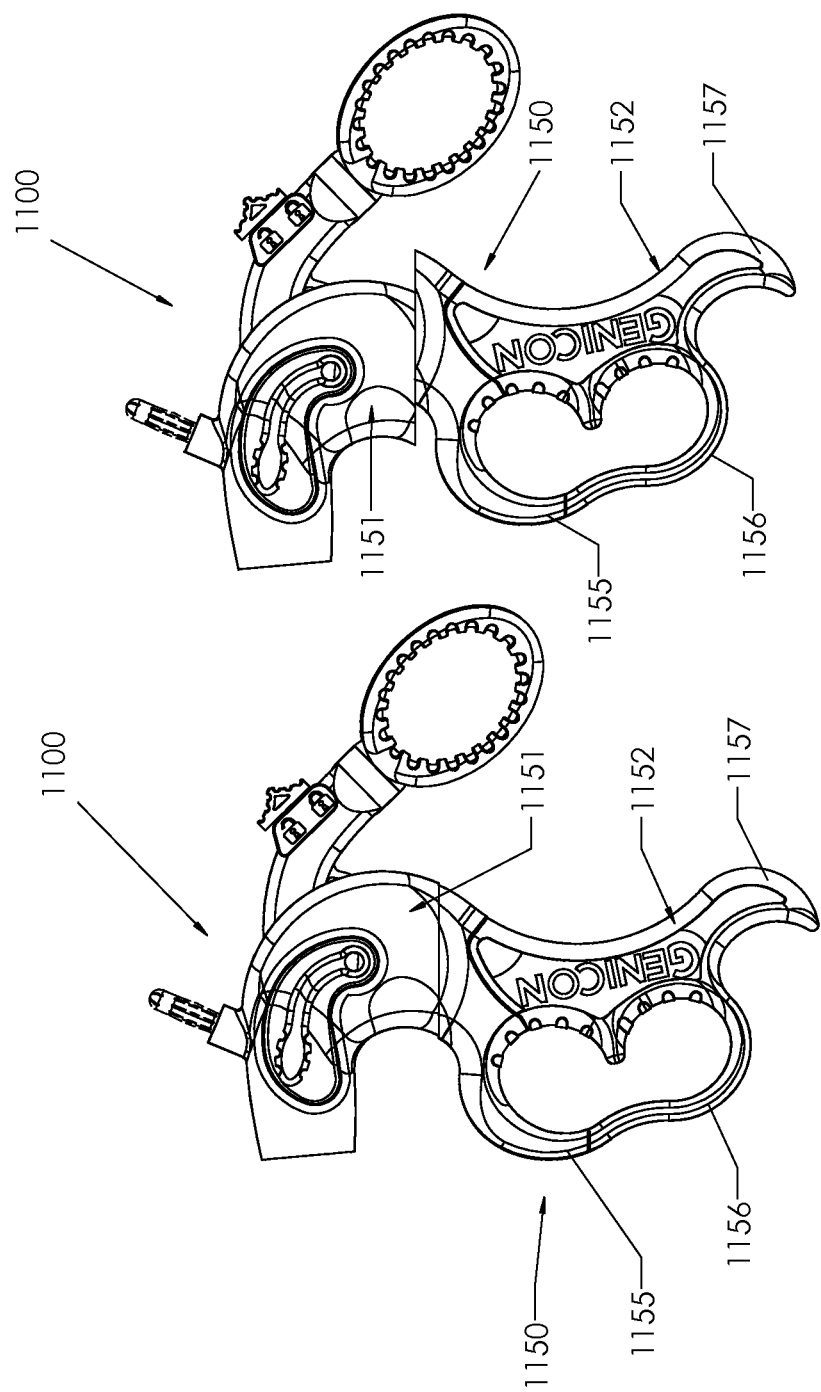
FIG. 22 is a perspective view illustrating a non-limiting exemplary embodiment including a bifurcated body having a lower portion adjustably coupled to a upper portion thereof.

FIG. 22 is a perspective view illustrating a non-limiting exemplary embodiment of the handle 1100 including a bifurcated body 1150 having a lower portion 1152 adjustably coupled to an upper portion 1151 thereof. FIG. 22A is a perspective view illustrating the lower portion 1152 of FIG. 22 linearly displaced relative to the upper portion 1151. In such an embodiment, the bifurcated region is located intermediately of the secondary digit-receiving member 1155, 1156 and the tertiary digit-supporting member 1157. The connection between the upper portion 1151 and lower portion 1152 of the body 1150 may be friction fitted, such as a snap-fit arrangement or via a detent, for example. A linearly resilient coupling may also be employed for causing the lower portion 1151 to automatically return to an equilibrium position from a tensioned position. Additionally a worm gear or other suitable mechanical and/or electromechanical mechanism may be employed. It is noted that the lower portion 1152 of the body 1150 can be articulated about x, y and z axes (e.g., ball/socket joint). Of course, the upper portion 1151 may move relative to a stationary lower portion 1152 as well.

Figure 23:
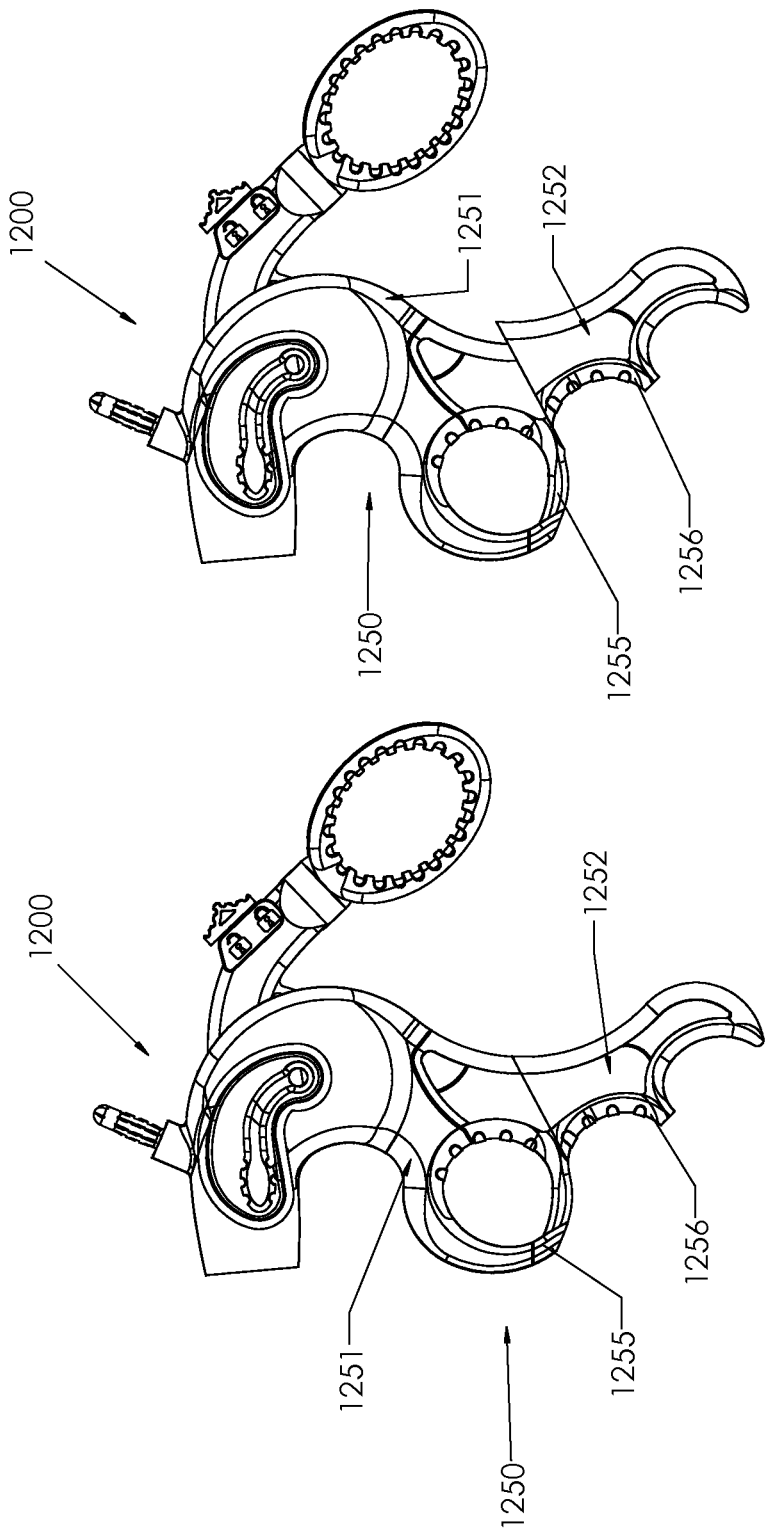
FIG. 23 is a perspective view illustrating a non-limiting exemplary embodiment including a bifurcated body having a lower portion adjustably coupled to a upper portion thereof.

FIG. 23 is a perspective view illustrating a non-limiting exemplary embodiment of handle 1200 including a bifurcated body 1250 having a lower portion 1252 adjustably coupled to a upper portion 1251 thereof. FIG. 23A is a perspective view illustrating the lower portion 1252 of FIG. 23 linearly displaced relative to the upper portion 1251. In such an embodiment, the bifurcated region separates the secondary digit-receiving members 1255, 1256 from each other. The connection between the upper portion 1251 and lower portion 1252 of the body 1250 may be friction fitted, such as a snap-fit arrangement or via a detent, for example. A linearly resilient coupling may also be employed for causing the lower portion 1252 to automatically return to an equilibrium position from a tensioned position. Additionally a worm gear or other suitable mechanical and/or electromechanical mechanism may be employed. It is noted that the lower portion 1252 of the body 1250 can be articulated about x, y and z axes (e.g., ball/socket joint). Of course, the upper portion 1251 may move relative to a stationary lower portion 1252 as well.

Figure 24:
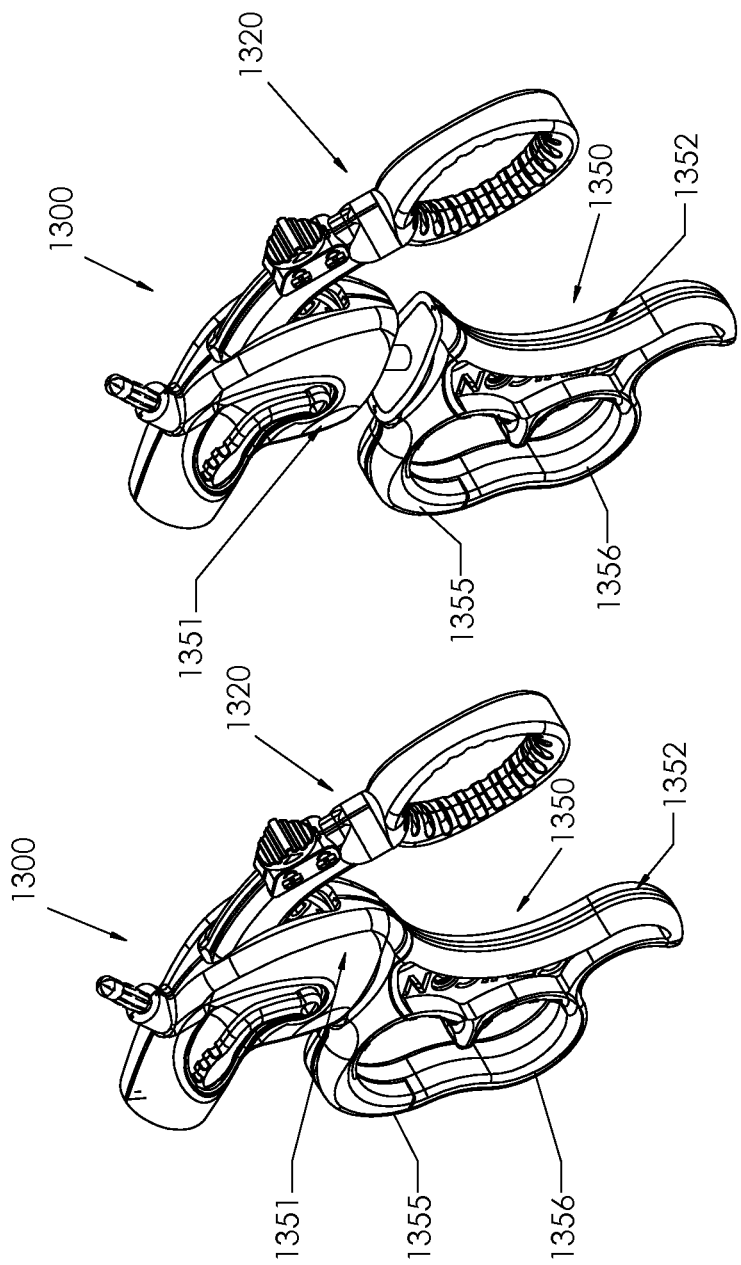
FIG. 24 is a perspective view illustrating a non-limiting exemplary embodiment including a bifurcated body having a lower portion adjustably coupled to a upper portion thereof.

FIG. 24 is a perspective view illustrating a non-limiting exemplary embodiment of handle 1300 including a bifurcated body 1350 having a lower portion 1352 adjustably coupled to an upper portion 1351 thereof. FIG. 24A is a perspective view illustrating the upper portion 1351 of FIG. 24 linearly displaced relative to the lower portion 1352. In such an embodiment, the bifurcated region is located intermediately of the first trigger assembly 1320 and secondary digit-supporting members 1355, 1356. The connection between the upper portion 1351 and lower portion 1352 of the body 1350 may be friction fitted, such as a snap-fit arrangement or via a detent, for example. A linearly resilient coupling may also be employed for causing the lower portion 1352 to automatically return to an equilibrium position from a tensioned position. Additionally a worm gear or other suitable mechanical and/or electromechanical mechanism may be employed. It is noted that the lower portion 1352 of the body 150 can be articulated about x, y and z axes (e.g., ball/socket joint). Of course, the upper portion 1351 may move relative to a stationary lower portion 1352 as well.

Figure 25:
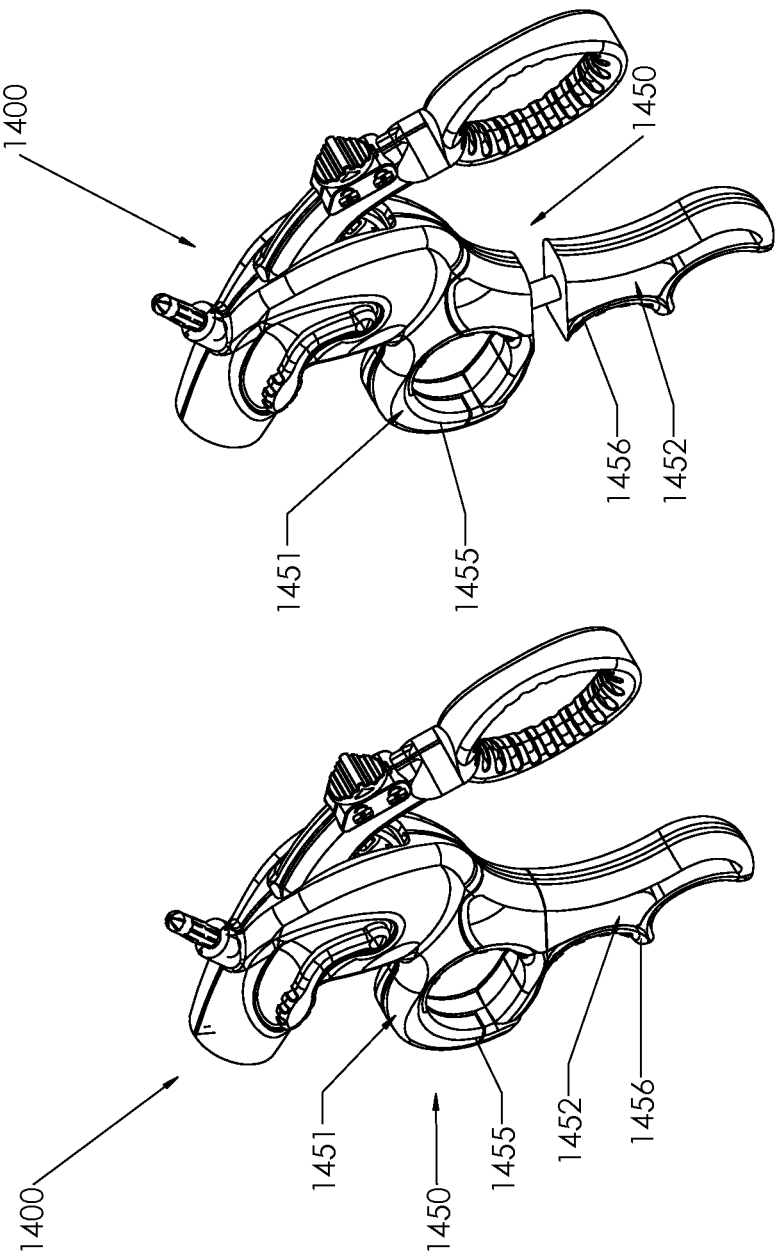
FIG. 25 is a perspective view illustrating a non-limiting exemplary embodiment including a bifurcated body having a lower portion adjustably coupled to a upper portion thereof.

FIG. 25 is a perspective view illustrating a non-limiting exemplary embodiment of handle 1400 including a bifurcated body 1450 having a lower portion 1452 adjustably coupled to an upper portion 1451 thereof. FIG. 25A is a perspective view illustrating the lower portion 1452 of FIG. 25 linearly displaced relative to the upper portion 1451. In such an embodiment, the bifurcated region separates the secondary digit-receiving members 1455, 1456 from each other. The connection between the upper portion 1451 and lower portion 1452 of the body 1450 may be friction fitted, such as a snap-fit arrangement or via a detent, for example. A linearly resilient coupling may also be employed for causing the lower portion 1452 to automatically return to an equilibrium position from a tensioned position. Additionally a worm gear or other suitable mechanical and/or electromechanical mechanism may be employed. It is noted that the lower portion 1452 of the body 1450 can be articulated about x, y and z axes (e.g., ball/socket joint). Of course, the upper portion 1451 may move relative to a stationary lower portion 1452 as well.

Figure 26:
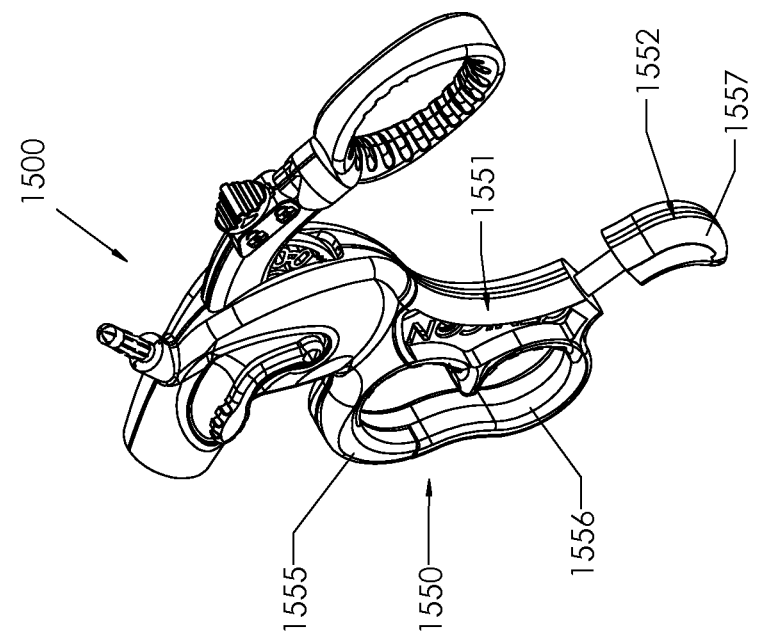
FIG. 26 is a perspective view illustrating a non-limiting exemplary embodiment including a bifurcated body having a lower portion adjustably coupled to a upper portion thereof.
Figure 26A:
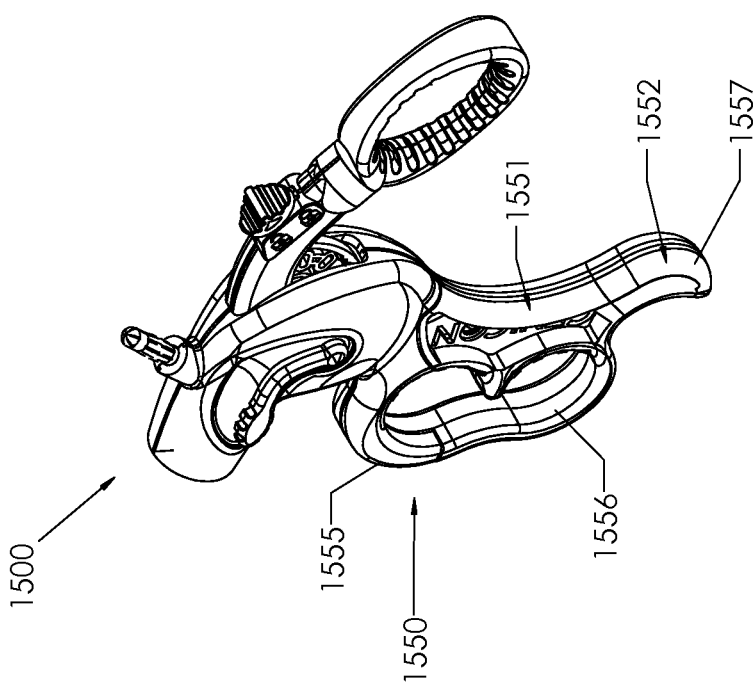
FIG. 26A is a perspective view illustrating the lower portion of FIG. 26 linearly displaced relative to the upper portion.

FIG. 26 is a perspective view illustrating a non-limiting exemplary embodiment of handle 1500 including a bifurcated body 1550 having a lower portion 1552 adjustably coupled to an upper portion 1551 thereof. FIG. 26A is a perspective view illustrating the lower portion 1552 of FIG. 26 linearly displaced relative to the upper portion 1551. In such an embodiment, the bifurcated region is located intermediately of the secondary digit-receiving members 1555, 1556 and the tertiary digit-supporting member 1557. The connection between the upper portion 1551 and lower portion 1552 of the body 1550 may be friction fitted, such as a snap-fit arrangement or via a detent, for example. A linearly resilient coupling may also be employed for causing the lower portion 1552 to automatically return to an equilibrium position from a tensioned position. Additionally a worm gear or other suitable mechanical and/or electromechanical mechanism may be employed. It is noted that the lower portion 1552 of the body 1550 can be articulated about x, y and z axes (e.g., ball/socket joint). Of course, the upper portion 1551 may move relative to a stationary lower portion 1552 as well.

Referring to FIGS. 27-28A, a non-limiting exemplary embodiment of the handle 1600 is illustrated wherein at least a portion of the second trigger assembly is removed from the body 1650 and non-operable such that the actuation arm 1629 freely articulates along an arcuate path 1612 without selectively locking at alternate positions.

While non-limiting exemplary embodiment(s) has/have been described with respect to certain specific embodiment(s), it will be appreciated that many modifications and changes may be made by those of ordinary skill in the relevant art(s) without departing from the true spirit and scope of the present disclosure. It is intended, therefore, by the appended claims to cover all such modifications and changes that fall within the true spirit and scope of the present disclosure. In particular, with respect to the above description, it is to be realized that the optimum dimensional relationships for the parts of the non-limiting exemplary embodiment(s) may include variations in size, materials, shape, form, function and manner of operation.

The Abstract of the Disclosure is provided to comply with 37 C.F.R. § 1.72(b) and is submitted with the understanding that it will not be used to interpret or limit the scope or meaning of the claims. In addition, in the above Detailed Description, various features may have been grouped together or described in a single embodiment for the purpose of streamlining the disclosure. This disclosure is not to be interpreted as reflecting an intention that the claimed embodiment(s) require more features than are expressly recited in each claim. Rather, as the following claims reflect, inventive subject matter may be directed to less than all of the features of any of the disclosed non-limiting exemplary embodiment(s). Thus, the following claims are incorporated into the Detailed Description, with each claim standing on its own as defining separately claimed subject matter.

The above disclosed subject matter is to be considered illustrative, and not restrictive, and the appended claims are intended to cover all such modifications, enhancements, and other embodiment(s) which fall within the true spirit and scope of the present disclosure. Thus, to the maximum extent allowed by law, the scope of the present disclosure is to be determined by the broadest permissible interpretation of the following claims and their equivalents, and shall not be restricted or limited by the above detailed description.

What is claimed as new and what is desired to secure by Letters Patent of the United States is:

1. A multi-functional handle for manipulating operation of a medical instrument, said multi-functional handle comprising:
    a body having a centrally-registered longitudinal plane and capable of being gripped;
    a first trigger assembly coupled to said body and comprising
        an actuation arm, and
        a primary digit-receiving member in communication with said actuation arm;
    wherein said primary digit-receiving member is selectively displaced between alternate orientations relative to a position of said body and relative to a position of said actuation arm, respectively; and
    a second trigger assembly operatively coupled to said first trigger assembly in such a manner that said actuation arm is selectively locked at alternate positions generally coplanar with the centrally-registered longitudinal plane of said body.

2. The multi-functional handle of claim 1, wherein said first trigger assembly is pivotal about a first pivot axis, wherein said second trigger assembly is pivotal about a second pivot axis, wherein each of said first and second pivot axes are offset and traverse the centrally-registered longitudinal plane of said body.

3. The multi-functional handle of claim 2, wherein said primary digit-receiving member is simultaneously displaced relative to said actuation arm while said first trigger assembly is articulated about said first pivot axis.

4. The multi-functional handle of claim 1, wherein said primary digit-receiving member is adjustably positioned about a proximal end of said actuation arm.

5. The multi-functional handle of claim 1, wherein said actuation arm is displaced along a first path generally coplanar with the centrally-registered longitudinal plane of said body.

6. The multi-functional handle of claim 1, wherein said primary digit-receiving member is a loop capable of receiving a digit of the user while the user grasps said body.

7. The multi-functional handle of claim 1, wherein said primary digit-receiving member is an incomplete loop capable of receiving a digit of the user while the user grasps said body.

8. The multi-functional handle of claim 1, wherein said primary digit-receiving member has a linear shape capable of supporting a digit of the user while the user grasps said body and said actuation arm is articulated along a first path.

9. The multi-functional handle of claim 1, wherein said primary digit-receiving member is registered parallel to the centrally-registered longitudinal plane of said body.

10. The multi-functional handle of claim 1, wherein said primary digit-receiving member is registered oblique to the centrally-registered longitudinal plane of said body.

11. The multi-functional handle of claim 1, wherein said primary digit-receiving member is registered orthogonal to the centrally-registered longitudinal plane of said body.

12. A multi-functional handle for manipulating operation of a medical instrument, said multi-functional handle comprising:
    a body having a centrally-registered longitudinal plane and capable of being gripped by a hand of a user;
    a first trigger assembly in communication with said body and comprising
        an actuation arm, and
        a primary digit-receiving member in communication with said actuation arm, said actuation arm being capable of actuating a medical instrument independently from movement of said primary digit-receiving member;
    wherein said primary digit-receiving member is selectively displaced between alternate orientations relative to a position of said body and relative to a position of said actuation arm, respectively; and
    a second trigger assembly operatively coupled to said first trigger assembly in such a manner that said actuation arm is selectively displaced at alternate positions generally coplanar with the centrally-registered longitudinal plane of said body;
    wherein said actuation arm includes a ratchet arm statically connected thereto.

13. The multi-functional handle of claim 12, wherein said ratchet arm is monolithically formed with said actuation arm.

14. The multi-functional handle of claim 12, wherein said ratchet arm is coplanar with said centrally-registered longitudinal plane of said body.

15. The multi-functional handle of claim 12, wherein said ratchet arm is integrally mated to said actuation arm.

16. The multi-functional handle of claim 12, wherein said ratchet arm remains fixedly coupled to said actuation arm during articulation of said first trigger assembly.

17. The multi-functional handle of claim 12, wherein articulation of said second trigger assembly from a first position to a second position permits articulation of said first trigger assembly along a first path; wherein articulation of said second trigger assembly from said second position to said first position prohibits articulation of said first trigger assembly along said first path.

18. The multi-functional handle of claim 17, wherein said ratchet arm is permitted from moving in sync with said actuation arm when said second trigger assembly is displaced to said first position.

19. The multi-functional handle of claim 12, wherein said second trigger assembly is selectively engaged to said actuation arm.

20. The multi-functional handle of claim 12, wherein said first trigger assembly is continuously engaged to said actuation arm.

\* \* \* \* \*